(12) United States Patent
Breu et al.

(10) Patent No.: US 6,242,601 B1
(45) Date of Patent: Jun. 5, 2001

(54) HETEROCYCLIC SULFAMIDES

(75) Inventors: Volker Breu, Schliengen (DE); Philippe Coassolo, Wittenheim (FR); Rolf Huber, Rheinfelden (CH); Werner Neidhart, Hagenthal le Bas (FR); Henri Ramuz, Birsfelden; Sébastien Roux, Basel, both of (CH); Hans Peter Wessel, Heitersheim (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/482,810

(22) Filed: Jan. 13, 2000

(30) Foreign Application Priority Data

Jan. 18, 1999 (EP) .................................. 99100784

(51) Int. Cl.$^7$ ............................................. C07D 239/28
(52) U.S. Cl. ................................................ 544/314
(58) Field of Search ............................... 544/314

(56) References Cited

U.S. PATENT DOCUMENTS 5,837,708    11/1998    Breu et al. ..................... 514/274

FOREIGN PATENT DOCUMENTS

| 0 713 875 | 11/1995 | (EP) . |
| 96/16963 * | 6/1996 | (WO) . |
| 96/19459 | 6/1996 | (WO) . |
| WO 97 22595 | 6/1997 | (WO) . |

OTHER PUBLICATIONS

Roux et al., Endothelin Antagonist Ro 61–1790, vol. 283, pp. 1110–1118 (1997).

* cited by examiner

*Primary Examiner*—Mukund J. Shah
*Assistant Examiner*—Hong Liu
(74) *Attorney, Agent, or Firm*—George W. Johnston; William H. Epstein; John P. Parise

(57) ABSTRACT

The compounds of formula (I)

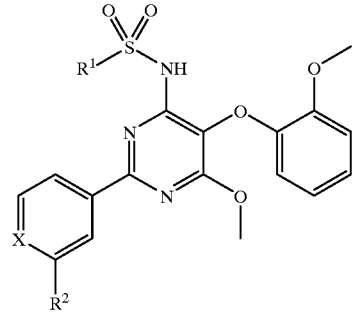

wherein $R^1$, $R^2$ and X have the significance as given in the description, are inhibitors of endothelin receptors and can therefore be used for the treatment of disorders which are associated with abnormal vascular tone and endothelial dysfunction.

63 Claims, No Drawings

HETEROCYCLIC SULFAMIDES

BACKGROUND OF THE INVENTION

1. Field

The present invention relates to heterocyclic sulfonamides and their use as medicaments.

2. Description

The publications EP 0 713 875 and EP 0 799 209 disclose sulfonamide compounds as endothelin receptor inhibitors. However, there is an art felt need for compounds having high antagonistic potency and high plasma levels following oral administration that lead to enhanced efficacy after oral administration.

SUMMARY OF THE INVENTION

The subject invention provides compounds of formula:

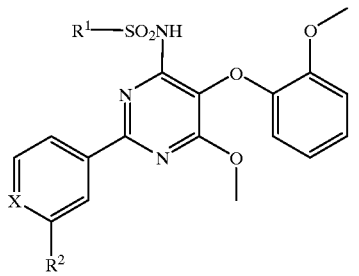

(I)

wherein $R^1$ is pyridyl, pyridyl substituted with halogen, lower alkyl, hydroxy-lower alkyl or lower alkenyl, pyrrolyl, pyrrolyl substituted with halogen, lower alkyl, hydroxy-lower alkyl or lower alkenyl, imidazolyl, imidazolyl substituted with halogen, lower alkyl, hydroxy-lower alkyl or lower alkenyl, thiazolyl, thiazolyl substituted with halogen, lower alkyl, hydroxy-lower alkyl or lower alkenyl, thiazolinyl, thiazolinyl substituted with halogen, lower alkyl, hydroxy-lower alkyl or lower alkenyl, oxazolyl, or oxazolyl substituted with halogen, lower alkyl, hydroxy-lower alkyl or lower alkenyl;

$R^2$ is $R^{21}$, —Y—$R^{22}$, heterocyclyl, or heterocyclyl that is mono-, di- or tri-substituted, independently, with hydroxy, lower alkenyl, amino, lower alkanoylamino, lower alkoxycarbonylamino, lower alkyl or hydroxy-lower alkyl;

$R^{21}$ is cyano, hydroxy-lower alkyl, carboxy, —C(O)NR$^a$R$^b$, —(CH$_2$)$_{1-4}$NHR$^c$, —(CH$_2$)$_{1-4}$NHC(O)NH(CH$_2$)$_{0-3}$CH$_3$, amidino, hydroxyamidino, lower alkoxycarbonyl or hydroxy-lower alkoxycarbonyl;

$R^{22}$ is hydrogen, lower alkanoyl, carboxy-lower alkyl, lower alkoxycarbonyl, lower alkoxycarbonyl-lower alkyl, carbamoyl-lower alkyl, di-lower alkylcarbamoyl-lower alkyl, allyl, lower alkyl or hydroxy-lower alkyl;

$R^a$ is hydrogen, lower alkyl, or lower alkyl substituted with hydroxy or lower alkoxy;

$R^b$ is hydrogen or lower alkyl;

$R^c$ is hydrogen, acetyl or lower alkylsulfonyl;

X is —CH— or —N—; and

Y is —O—, —NH—;

and pharmaceutically acceptable salts and esters thereof.

While all combinations of the above-mentioned substituents are envisioned, certain substituents are favored. For example, where $R^1$ is pyridyl, pyridyl substituted with halogen, lower alkyl, hydroxy-lower alkyl or lower alkenyl, thiazolyl, or thiazolyl substituted with halogen, lower alkyl, hydroxy-lower alkyl or lower alkenyl. More preferred is where $R^1$ is pyridyl, pyridyl substituted with lower alkyl or lower alkenyl, thiazolyl, or thiazolyl substituted with lower alkyl or lower alkenyl.

When $R^2$ is $R^{21}$, preferred compounds are where $R^{21}$ is cyano, hydroxy-lower alkyl, carboxy, lower alkoxycarbonyl, —C(O)NR$^a$R$^b$, —CH$_2$NHR$^c$, amidino, hydroxyamidino or —CH$_2$NHC(O)NHCH$_2$CH$_3$, and $R^a$, $R^b$ and $R^c$ are as defined above. More preferred compounds are where $R^{21}$ is cyano, carboxy, carbamoyl, lower alkoxycarbonyl, hydroxy-lower alkyl, acetylaminomethyl or methylsulfonylaminomethyl.

Another favored group of compounds are those where $R^2$ is $R^{21}$, —Y—$R^{22}$ or heterocyclyl selected from the group consisting of 2-pyrimidinyl, 2-imidazolyl, [1,2,4]oxadiazol-3-yl, 2-oxazolyl or 2-thiazolyl, 2-pyrimidinyl mono-, di- or tri-substituted, independently, with lower alkyl, hydroxy-lower alkyl, lower alkenyl, lower alkoxycarbonylamino, lower alkanoylamino, hydroxy or amino, 2-imidazolyl mono-, di- or tri-substituted, independently, with lower alkyl, hydroxy-lower alkyl, lower alkenyl, lower alkoxycarbonylamino, lower alkanoylamino, hydroxy or amino, [1,2,4]oxadiazol-3-yl mono-, di- or tri-substituted, independently, with lower alkyl, hydroxy-lower alkyl, lower alkenyl, lower alkoxycarbonylamino, lower alkanoylamino, hydroxy or amino, 2-oxazolyl mono-, di- or tri-substituted, independently, with lower alkyl, hydroxy-lower alkyl, lower alkenyl, lower alkoxycarbonylamino, lower alkanoylamino, hydroxy or amino, and 2-thiazolyl mono-, di- or tri-substituted, independently, with lower alkyl, hydroxy-lower alkyl, lower alkenyl, lower alkoxycarbonylamino, lower alkanoylamino, hydroxy or amino. More preferred compounds include those where $R^2$ is $R^{21}$, —Y—$R^{22}$ or heterocyclyl selected from the group consisting of 2-pyrimidinyl, 2-imidazolyl, [1,2,4]oxadiazol-3-yl, 2-pyrimidinyl substituted with lower alkyl, isopropenyl, t-butoxycarbonylamino, formylamino, acetylamino, hydroxy, amino or hydroxymethyl, 2-imidazolyl substituted with lower alkyl, isopropenyl, t-butoxycarbonylamino, formylamino, acetylamino, hydroxy, amino or hydroxymethyl, and [1,2,4]oxadiazol-3-yl substituted with lower alkyl, isopropenyl, t-butoxycarbonylamino, formylamino, acetylamino, hydroxy, amino or hydroxymethyl.

Yet another group of favored compounds are those where $R^2$ is $R^{22}$ and $R^{22}$ is hydrogen, lower alkyl, carboxymethyl, lower alkoxycarbonyl-lower alkyl, carbamoylmethyl, dimethylcarbamoylmethyl, hydroxy-lower alkyl or acetyl. Preferred are where $R^{22}$ is hydrogen, lower alkyl, lower alkoxycarbonyl-lower alkyl or hydroxy-lower alkyl.

A special category of compounds are those of the formula:

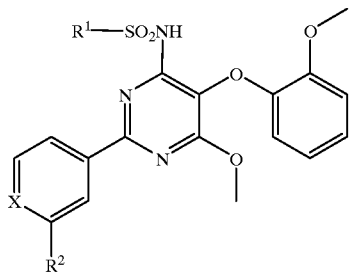

(I)

wherein
R¹ is pyridyl or pyridyl substituted with lower alkyl;
R² is hydroxy, carboxy or methoxycarbonyl; and
X is —CH— or —N—;
and pharmaceutically acceptable salts and esters thereof.

R¹ is favorably pyridyl substituted with lower alkyl, preferably methylpyridyl and specifically R¹ is 5-methyl-pyridine-2-yl.

R² may favorably be hydroxy, especially where X is —CH—.

X can also be —N—. In such cases, it is favored when R² is carboxy or methoxycarbonyl.

DETAILED DESCRIPTION OF THE PREFERRED EMBODIMENTS

The subject invention will now be described in terms of its preferred embodiments. These embodiments are set forth to aid in understanding the invention but are not to be construed as limiting the invention.

The present invention relates to compounds of the formula (I)

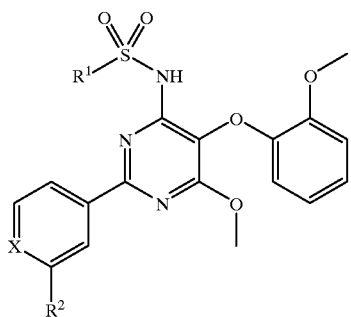

(I)

wherein
R¹ is pyridyl, pyrrolyl, imidazolyl, thiazolyl, thiazolinyl or oxazolyl, optionally substituted with halogen, lower alkyl, hydroxy-lower alkyl or lower alkenyl;
R² is $R^{21}$, —Y—$R^{22}$ or heterocyclyl, wherein heterocyclyl may optionally be mono-, di- or tri-substituted, independently, with hydroxy, lower alkenyl, amino, lower alkanoylamino, lower alkoxycarbonylamino, lower alkyl or hydroxy-lower alkyl;
$R^{21}$ is cyano, hydroxy-lower alkyl, carboxy, —C(O)NR$^a$R$^b$, —(CH$_2$)$_{1-4}$NHR$^c$, —(CH$_2$)$_{1-4}$NHC(O)NH(CH$_2$)$_{0-3}$CH$_3$, amidino, hydroxyamidino, lower alkoxycarbonyl or hydroxy-lower alkoxycarbonyl;
$R^{22}$ is hydrogen, lower alkanoyl, carboxy-lower alkyl, lower alkoxycarbonyl, lower alkoxycarbonyl-lower alkyl, carbamoyl-lower alkyl, di-lower alkylcarbamoyl-lower alkyl, allyl, lower alkyl or hydroxy-lower alkyl;
$R^a$ is hydrogen or lower alkyl, optionally substituted with hydroxy or lower alkoxy;
$R^b$ is hydrogen or lower alkyl;
$R^c$ is hydrogen, acetyl or lower alkylsulfonyl;
X is —CH— or —N—; and
Y is —O—, —NH—;
and pharmaceutically acceptable salts and esters thereof.

The present invention also relates to a pharmaceutical composition comprising a compound of formula (I) and a pharmaceutically acceptable carrier and/or adjuvant.

Furthermore, the present invention relates to the use of such compounds for the preparation of medicaments for the treatment and/or prophylaxis of disorders that are associated with abnormal vascular tone and endothelial dysfunction.

The present invention also relates to processes for the preparation of the compounds of formula (I).

In addition, the present invention relates to a method for the prophylactic and/or therapeutic treatment of disorders which are associated with abnormal vascular tone and endothelial dysfunction, which method comprises administering a compound of formula (I) to a human or an animal.

The sulfonamides of the present invention are inhibitors of endothelin receptors. They can accordingly be used for the treatment of disorders which are associated with abnormal vascular tone and endothelial dysfunction.

EP 0 713 875 and EP 0 799 209 disclose sulfonamide compounds as endothelin receptor inhibitors. However, the compounds of the present invention have a high antagonistic potency in vitro and show unexpectedly high plasma levels following oral administration, which leads to high in vivo efficacy after oral administration.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms.

The term "lower alkyl" refers to a branched or straight chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "lower alkenyl" refers to a lower alkyl group containing one or more double bond(s) in the alkylene chain.

The term "lower alkoxy" refers to the group —O—R', wherein R' is a lower alkyl.

The term "carboxy" refers to the group —C(O)OH.

The term "formylamino" refers to a formyl group attached to an imino radical, i.e. —NHC(O)H.

The term "lower alkanoyl" refers to the group —C(O)R', wherein R' is hydrogen or lower alkyl.

The term "lower alkanoylamino" refers to a lower alkanoyl group attached to an imino radical.

The term "carboxy-lower alkyl" refers to the group —R'—C(O)OH, wherein R' is a lower alkyl.

The term "lower alkoxycarbonyl" refers to the group —C(O)—R', wherein R' is a lower alkoxy.

The term "lower alkoxycarbonyl-lower alkyl" refers to the group —R'—C(O)—R", wherein R' is a lower alkyl and R" is a lower alkoxy.

The term "carbamoyl-lower alkyl" refers to the group —R'—C(O)NH$_2$, wherein R' is a lower alkyl.

The term "di-lower alkylcarbamoyl-lower alkyl" refers to the group —R'—C(O)N(R")R'", wherein R', R" and R'" denote each an independently selected lower alkyl group.

The term "acetyl" refers to the group —COCH$_3$.

The term "acetylamino" refers to the group —NHCOCH$_3$.

The term "lower alkylsulfonyl" refers to the group —SO$_2$—R', wherein R' is lower alkyl.

The term "heterocyclyl" refers to an unsaturated or aromatic, preferably aromatic, monovalent 5- or 6-membered carbocyclic radical having at least one heteroatom, i.e. nitrogen, oxygen or sulfur, or a combination thereof. Examples of such heterocyclyl residues are pyrimidinyl, imidazolyl, oxadiazolyl, oxazolyl and thiazolyl.

The term "halogen" refers to fluorine, chlorine, bromine and iodine, with chlorine being preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms. It also includes salts with inorganic or organic bases such as alkali salts like sodium and potassium salts, alkaline earth metal salts like calcium and magnesium salts, N-methyl-D-glutamine salts and salts with amino acids like arginine, lysine and the like.

More particularly, the present invention relates to compounds of the above formula (I), wherein $R^1$ is pyridyl, pyrrolyl, imidazolyl, thiazolyl, thiazolinyl or oxazolyl, optionally substituted with halogen, lower alkyl, hydroxy-lower alkyl or lower alkenyl. In $R^1$ the term "lower alkyl" preferably means methyl, ethyl, n-propyl, isopropyl, n-butyl, s-butyl or t-butyl, more preferably methyl, isopropyl or t-butyl, most preferably methyl or isopropyl. The term "hydroxy-lower alkyl" preferably means hydroxymethyl, hydroxyethyl, hydroxypropyl, hydroxybutyl or —C(CH$_3$)$_2$OH, more preferably hydroxymethyl or —C(CH$_3$)$_2$OH. The term "lower alkenyl" preferably means vinyl, 1-propenyl, allyl, isopropenyl, 1-butenyl, 2-butenyl or 3-butenyl, more preferably isopropenyl.

Preferred residues $R^1$ are pyridyl or thiazolyl, optionally substituted with halogen, lower alkyl, hydroxy-lower alkyl or lower alkenyl. More preferred are pyridyl or thiazolyl, optionally substituted with lower alkyl, e.g. methyl or isopropyl, or lower alkenyl, e.g. isopropenyl. Most preferred are 5-methyl-pyridine-2-yl, 5-isopropyl-pyridine-2-yl, 5-isopropenyl-pyridine-2-yl and 5-methyl-thiazol-2-yl.

$R^2$ is $R^{21}$, —Y—$R^{22}$ or heterocyclyl, wherein heterocyclyl may optionally be mono-, di- or tri-substituted, independently, with hydroxy, lower alkenyl, amino, lower alkanoylamino, lower alkoxycarbonylamino, lower alkyl or hydroxy-lower alkyl. In the definitions of the substituents of the heterocyclyl residues in $R^2$ the term "lower alkenyl" preferably means vinyl, 1-propenyl, allyl, 1-butenyl, 2-butenyl or 3-butenyl, more preferably allyl. The term "lower alkanoylamino" preferably means formylamino, acetylamino or propionylamino, more preferably formylamino or acetylamino. The term "lower alkoxycarbonylamino" preferably means methoxycarbonylamino, ethoxycarbonylamino, n-propoxycarbonylamino, i-propoxycarbonylamino, n-butoxycarbonylamino, i-butoxycarbonylamino or t-butoxycarbonylamino, more preferably t-butoxycarbonylamino. The term "lower alkyl" preferably means methyl, ethyl, n-propyl, isopropyl, n-butyl, s-butyl or t-butyl, more preferably methyl, ethyl or isopropyl, most preferably methyl. The term "hydroxy-lower alkyl" preferably means hydroxymethyl, hydroxyethyl, hydroxypropyl or hydroxybutyl, more preferably hydroxymethyl.

Preferred heterocyclyl residues in $R^2$ are 2-pyrimidinyl, 2-imidazolyl, [1,2,4]oxadiazol-3-yl, 2-oxazolyl and 2-thiazolyl, more preferred are 2-pyrimidinyl, 2-imidazolyl and [1,2,4]oxadiazol-3-yl, most preferred is [1,2,4] oxadiazol-3-yl. These heterocyclyl residues in $R^2$ may optionally be mono-, di- or tri-substituted, independently, with lower alkyl, hydroxy-lower alkyl, lower alkenyl, lower alkoxycarbonylamino, lower alkanoylamino, hydroxy or amino, preferably with lower alkyl, e.g. methyl, isopropenyl, t-butoxycarbonylamino, formylamino, acetylamino, hydroxy, amino or hydroxymethyl, more preferably with lower alkyl, e.g. methyl, or hydroxy. Most preferred heterocyclyl residue in $R^2$ is [1,2,4]oxadiazol-3-yl, optionally substituted with hydroxy or lower alkyl, e.g. methyl.

$R^{21}$ is cyano, hydroxy-lower alkyl, carboxy, —C(O)NR$^a$R$^b$, —(CH$_2$)$_{1-4}$NHR$^c$, —(CH$_2$)$_{1-4}$NHC(O)NH (CH$_2$)$_{0-3}$CH$_3$, amidino, hydroxyamidino, lower alkoxycarbonyl or hydroxy-lower alkoxycarbonyl. In $R^{21}$ the term "hydroxy-lower alkyl" preferably means hydroxymethyl, 1-hydroxyethyl or 2-hydroxyethyl, more preferably hydroxymethyl. The term "—(CH$_2$)$_{1-4}$NHC(O)NH (CH$_2$)$_{0-3}$CH$_3$" preferably means —CH$_2$NHC(O) NHCH$_2$CH$_3$. The term "lower alkoxycarbonyl" preferably means methoxycarbonyl, ethoxycarbonyl, n-propoxycarbonyl, i-propoxycarbonyl, n-butoxycarbonyl, s-butoxycarbonyl or t-butoxycarbonyl, more preferably methoxycarbonyl or ethoxycarbonyl. The term "hydroxy-lower alkoxycarbonyl" preferably means 2-hydroxyethoxycarbonyl and 3-hydroxypropyloxycarbonyl, preferably 2-hydroxyethoxycarbonyl.

Preferred substituents $R^{21}$ are cyano, hydroxy-lower alkyl, e.g. hydroxymethyl, carboxy, lower alkoxycarbonyl, e.g. methoxycarbonyl or ethoxycarbonyl, —C(O)NR$^a$R$^b$, —CH$_2$NHR$^c$, amidino, hydroxyamidino or —CH$_2$NHC(O) NHCH$_2$CH$_3$, wherein R$^a$, R$^b$ and R$^c$ are as defined in claim 1. Most preferred are cyano, carboxy, carbamoyl, lower alkoxycarbonyl, e.g. methoxycarbonyl or ethoxycarbonyl, acetylaminomethyl, methylsulfonylaminomethyl or hydroxy-lower alkyl, e.g. hydroxymethyl.

$R^{22}$ is hydrogen, lower alkanoyl, carboxy-lower alkyl, lower alkoxycarbonyl, lower alkoxycarbonyl-lower alkyl, carbamoyl-lower alkyl, di-lower alkylcarbamoyl-lower alkyl, allyl, lower alkyl or hydroxy-lower alkyl. In $R^{22}$ the term "lower alkanoyl" preferably means acetyl, propionyl or butyryl, more preferably acetyl. The term "carboxy-lower alkyl" preferably means carboxymethyl, carboxyethyl, carboxypropyl or carboxybutyl, more preferably carboxymethyl. The term "lower alkoxycarbonyl" preferably means methoxycarbonyl, ethoxycarbonyl, n-propoxycarbonyl, i-propoxycarbonyl, n-butoxycarbonyl, s-butoxycarbonyl or t-butoxycarbonyl, more preferably n-propoxycarbonyl, i-propoxycarbonyl, n-butoxycarbonyl, s-butoxycarbonyl or t-butoxycarbonyl, most preferably t-butoxycarbonyl. The term "lower alkoxycarbonyl-lower alkyl" preferably means methoxycarbonylmethyl, ethoxycarbonylmethyl, methoxycarbonylethyl or ethoxycarbonylethyl, more preferably methoxycarbonylmethyl or ethoxycarbonylmethyl. The term "carbamoyl-lower alkyl" preferably means carbamoylmethyl, carbamoylethyl or carbamoylpropyl, more preferably carbamoylmethyl. The term "di-lower alkylcarbamoyl-lower alkyl" preferably means dimethylcarbamoylmethyl, ethyl-methylcarbamoylmethyl, dimethylcarbamoylethyl, ethyl-methylcarbamoylethyl or diethylcarbamoylmethyl, more preferably dimethylcarbamoylmethyl. The term "lower alkyl" preferably means methyl, ethyl, n-propyl, isopropyl, n-butyl, s-butyl or t-butyl, more preferably methyl or ethyl, most preferably methyl. The term "hydroxy-lower alkyl" preferably means hydroxyethyl or hydroxypropyl, more preferably hydroxyethyl.

Preferred substituents $R^{22}$ are hydrogen, lower alkyl, carboxymethyl, lower alkoxycarbonyl-lower alkyl, e.g. methoxycarbonylmethyl or ethoxycarbonylmethyl, carbamoylmethyl, dimethylcarbamoylmethyl, acetyl or hydroxy-lower alkyl, e.g. hydroxyethyl. Most preferred are hydrogen, lower alkyl, e.g. methyl, lower alkoxycarbonyl-lower alkyl, e.g. methoxycarbonylmethyl or ethoxycarbonylmethyl, or hydroxy-lower alkyl, e.g. hydroxyethyl.

Preferred embodiments of $R^2$ are the substituents $R^{21}$ and —Y—$R^{22}$.

$R^a$ is hydrogen or lower alkyl, optionally substituted with hydroxy or lower alkoxy. In $R^a$ the term "lower alkyl" preferably means methyl, ethyl, n-propyl, isopropyl, n-butyl, s-butyl or t-butyl, more preferably methyl or ethyl, most preferably methyl. The term "lower alkoxy" preferably means methoxy, ethoxy, propoxy or butoxy, most preferably methoxy.

Preferred substituents $R^a$ are hydrogen, methyl, ethyl, hydroxyethyl or methoxyethyl, most preferred are hydrogen or methyl.

$R^b$ is hydrogen or lower alkyl. In $R^b$ the term "lower alkyl" preferably means methyl, ethyl, n-propyl, isopropyl, n-butyl, s-butyl or t-butyl, more preferably methyl or ethyl, most preferably methyl.

Preferred substituents $R^b$ are hydrogen, methyl and ethyl, more preferred are hydrogen and methyl, most preferred is hydrogen.

$R^c$ is hydrogen, acetyl or lower alkylsulfonyl. In $R^c$ the term "lower alkylsulfonyl" preferably means methylsulfonyl, ethylsulfonyl, propylsulfonyl or butylsulfonyl, more preferably methylsulfonyl or ethylsulfonyl, most preferably methylsulfonyl.

Preferred substituents $R^c$ are acetyl or methylsulfonyl, most preferred is acetyl.

X is —CH— or —N—. In a preferred aspect, substituent X is —N—. In another preferred aspect, substituent X is —CH—.

Y is —O— or —NH—. In a preferred aspect, substituent Y is —O—.

Particularly preferred compounds of formula (I) are:

4-[4-methoxy-5-(2-methoxy-phenoxy)-6-(5-methyl-pyridine-2-sulfonylamino)-pyrimidin-2-yl]-pyridine-2-carboxylic acid, 4-[4-methoxy-5-(2-methoxy-phenoxy)-6-(5-methyl-pyridine-2-sulfonylamino)-pyrimidin-2-yl]-pyridine-2-carboxylic acid methyl ester, 5-methyl-pyridine-2-sulfonic acid [2-(2-hydroxymethyl-pyridine-4-yl)-6-methoxy-5-(2-methoxy-phenoxy)-pyrimidin-4-yl]-amide, 4-[4-methoxy-5-(2-methoxy-phenoxy)-6-(5-methyl-pyridine-2-sulfonylamino)-pyrimidin-2-yl]-pyridine-2-carboxylic acid ethyl ester, 4-[4-(5-isopropyl-pyridine-2-sulfonylamino)-6-methoxy-5-(2-methoxy-phenoxy)-pyrimidin-2-yl]-pyridine-2-carboxylic acid methyl ester, N-hydroxy-4-[4-methoxy-5-(2-methoxy-phenoxy)-6-(5-methyl-pyridine-2-sulfonylamino)-pyrimidin-2-yl]-pyridine-2-carboxamidine, 5-methyl-pyridine-2-sulfonic acid {6-methoxy-5-(2-methoxy-phenoxy)-2-[2-(5-methyl-[1,2,4]oxadiazol-3-yl)-pyridine-4-yl]-pyrimidin-4-yl}-amide, 5-methyl-pyridine-2-sulfonic acid [2-[2-(methanesulfonylamino-methyl)-pyridine-4-yl]-6-methoxy-5-(2-methoxy-phenoxy)-pyrimidin-4-yl]-amide, 5-isopropyl-pyridine-2-sulfonic acid [2-[2-(methanesulfonylamino-methyl)-pyridine-4-yl]-6-methoxy-5-(2-methoxy-phenoxy)-pyrimidin-4-yl]-amide, 5-isopropyl-pyridine-2-sulfonic acid {6-methoxy-5-(2-methoxy-phenoxy)-2-[2-(5-methyl-[1,2,4]oxadiazol-3-yl)-pyridine-4-yl]-pyrimidin-4-yl}-amide, 5-methyl-pyridine-2-sulfonic acid [2-(2-cyano-pyridine-4-yl)-6-methoxy-5-(2-methoxy-phenoxy)-pyrimidin-4-yl]-amide, 5-methyl-pyridine-2-sulfonic acid [2-(3-hydroxy-phenyl)-6-methoxy-5-(2-methoxy-phenoxy)-pyrimidin-4-yl]-amide, 5-methyl-pyridine-2-sulfonic acid [2-[3-(2-hydroxy-ethoxy)-phenyl]-6-methoxy-5-(2-methoxy-phenoxy)-pyrimidin-4-yl]-amide and 5-isopropyl-pyridine-2-sulfonic acid [2-[2-(2-hydroxy-ethoxy)-pyridine-4-yl]-6-methoxy-5-(2-methoxy-phenoxy)-pyrimidin-4-yl]-amide, 5-methyl-pyridine-2-sulfonic acid [2-(2-hydroxy-pyridin-4-yl)-6-methoxy-5-(2-methoxy-phenoxy)-pyrimidin-4-yl]-amide, {3-[4-methoxy-5-(2-methoxy-phenoxy)-6-(5-methyl-pyridine-2-sulfonylamino)-pyrimidin-2-yl]-phenoxy}-acetic acid ethyl ester, 5-isopropyl-pyridine-2-sulfonic acid [2-(2-hydroxymethyl-pyridin-4-yl)-6-methoxy-5-(2-methoxy-phenoxy)-pyrimidin-4-yl]-amide, N-{4-[4-(5-isopropyl-pyridine-2-sulfonylamino)-6-methoxy-5-(2-methoxy-phenoxy)-pyrimidin-2-yl]-pyridin-2-ylmethyl}-acetamide, 4-[4-(5-isopropyl-pyridine-2-sulfonylamino)-6-methoxy-5-(2-methoxy-phenoxy)-pyrimidin-2-yl]-pyridine-2-carboxylic acid, 4-[4-(5-isopropyl-pyridine-2-sulfonylamino)-6-methoxy-5-(2-methoxy-phenoxy)-pyrimidin-2-yl]-pyridine-2-carboxylic acid isopropyl ester, 4-[4-(5-isopropyl-pyridine-2-sulfonylamino)-6-methoxy-5-(2-methoxy-phenoxy)-pyrimidin-2-yl]-pyridine-2-carboxylic acid ethyl ester, 5-methyl-thiazole-2-sulfonic acid [2-[2-(2-hydroxy-ethoxy)-pyridin-4-yl]-6-methoxy-5-(2-methoxy-phenoxy)-pyrimidin-4-yl]-amide, 4-[4-(5-isopropyl-pyridine-2-sulfonylamino)-6-methoxy-5-(2-methoxy-phenoxy)-pyrimidin-2-yl]-pyridine-2-carboxylic acid amide, N-hydroxy-4-[4-(5-isopropyl-pyridine-2-sulfonylamino)-6-methoxy-5-(2-methoxy-phenoxy)-pyrimidin-2-yl]-pyridine-2-carboxamidine, Acetic acid 3-[4-methoxy-5-(2-methoxy-phenoxy)-6-(5-methyl-pyridine-2-sulfonylamino)-pyrimidin-2-yl]-phenyl ester, 4-[4-(5-isopropyl-pyridine-2-sulfonylamino)-6-methoxy-5-(2-methoxy-phenoxy)-pyrimidin-2-yl]-pyridine-2-carboxylic acid methyl ester and 4-[4-Methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

More particularly preferred compounds of formula (I) are:

5-methyl-pyridine-2-sulfonic acid [2-[3-(2-hydroxy-ethoxy)-phenyl]-6-methoxy-5-(2-methoxy-phenoxy)-pyrimidin-4-yl]-amide,
5-methyl-pyridine-2-sulfonic acid [2-(3-hydroxy-phenyl)-6-methoxy-5-(2-methoxy-phenoxy)-pyrimidin-4-yl]-amide,
5-methyl-pyridine-2-sulfonic acid [2-(2-cyano-pyridin-4-yl)-6-methoxy-5-(2-methoxy-phenoxy)-pyrimidin-4-yl]-amide,
4-[4-methoxy-5-(2-methoxy-phenoxy)-6-(5-methyl-pyridine-2-sulfonylamino)-pyrimidin-2-yl]-pyridine-2-carboxylic acid,
4-[4-methoxy-5-(2-methoxy-phenoxy)-6-(5-methyl-pyridine-2-sulfonylamino)-pyrimidin-2-yl]-pyridine-2-carboxylic acid methyl ester,
5-methyl-pyridine-2-sulfonic acid [2-(2-hydroxymethyl-pyridin-4-yl)-6-methoxy-5-(2-methoxy-phenoxy)-pyrimidin-4-yl]-amide,
4-[4-methoxy-5-(2-methoxy-phenoxy)-6-(5-methyl-pyridine-2-sulfonylamino)-pyrimidin-2-yl]-pyridine-2-carboxylic acid ethyl ester,
5-isopropyl-pyridine-2-sulfonic acid [2-(2-hydroxymethyl-pyridin-4-yl)-6-methoxy-5-(2-methoxy-phenoxy)-pyrimidin4-yl]-amide,
4-[4-(5-isopropyl-pyridine-2-sulfonylamino)-6-methoxy-5-(2-methoxy-phenoxy)-pyrimidin-2-yl]-pyridine-2-carboxylic acid amide,
4-[4-(5-isopropyl-pyridine-2-sulfonylamino)-6-methoxy-5-(2-methoxy-phenoxy)-pyrimidin-2-yl]-pyridine-2-carboxylic acid ethyl ester,
5-methyl-pyridine-2-sulfonic acid {6-methoxy-5-(2-methoxy-phenoxy)-2-[2-(5-methyl-[1,2,4]oxadiazol-3-yl)-pyridin-4-yl]-pyrimidin-4-yl}-amide and
4-[4-Methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

Most preferred compounds of formula (I) are:

4-[4-methoxy-5-(2-methoxy-phenoxy)-6-(5-methyl-pyridine-2-sulfonylamino)-pyrimidin-2-yl]-pyridine-2-carboxylic acid,
5-methyl-pyridine-2-sulfonic acid [2-(3-hydroxy-phenyl)-6-methoxy-5-(2-methoxy-phenoxy)-pyrimidin-4-yl]-amide,
5-methyl-pyridine-2-sulfonic acid [2-(2-hydroxymethyl-pyridin-4-yl)-6-methoxy-5-(2-methoxy-phenoxy)-pyrimidin-4-yl]-amide,
4-[4-Methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

The compounds of formula (I) can be prepared according to the following methods:

a) For the compounds with X=—N— in general formula (I), by reacting a compound of formula (II)—according to scheme 1—with a trialkylsilyl cyanide and a trialkylamine to give compound of general formula (Ia).

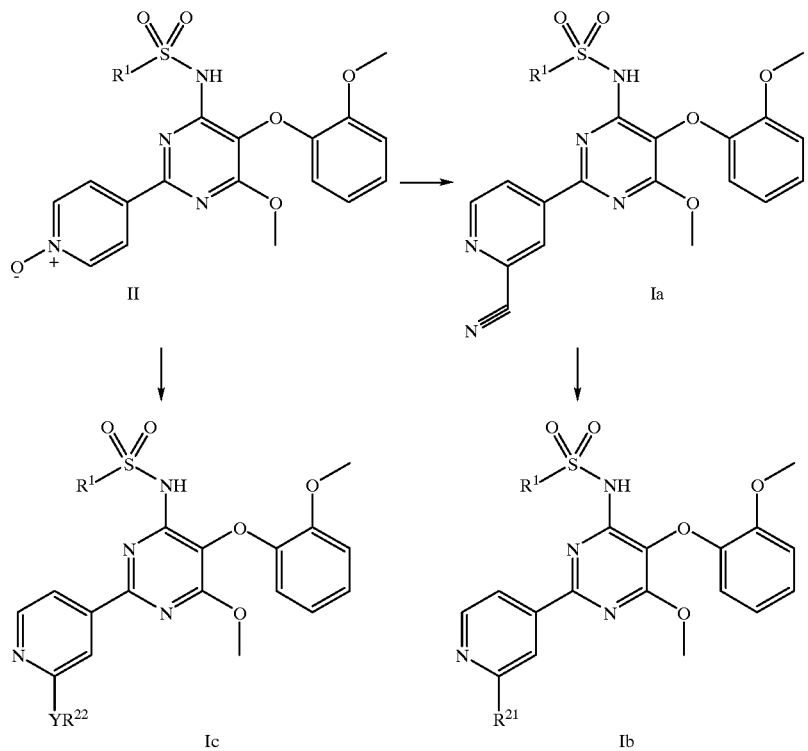

Scheme 1

Alternatively, compounds of general formula (Ia) can be prepared from compounds of formula (III)—according to scheme 1a—by treatment with sodium methylate in MeOH to give the corresponding iminoether intermediates of formula (IV) which can be further converted into compounds of formula (Ia) on treatment with a base such as NaH.

Scheme 1a

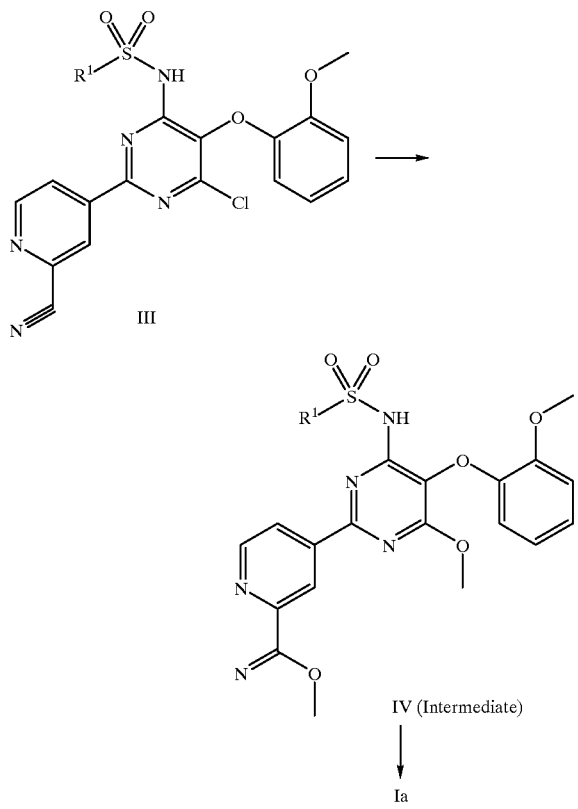

The cyano group in compounds of general formula (Ia) can be converted into a carbamoyl group by treatment with aqueous sodium hydroxide which can be further converted into carboxy on hydrolysis with aqueous diluted acid. Alternatively, the cyano group can be converted into alkoxyimino with sodium alkoxide which can be further reacted under aqueous acidic conditions in the presence of a suited alcohol to give alkoxycarbonyl or, under aqueous basic conditions, to yield carboxy. Methoxycarbonyl and carboxy can alternatively be obtained directly from the intermediate of formula (IV) as described above.

Hydroxy-lower alkoxycarbonyl or alkoxycarbonyl or a specifically functionalized alkoxycarbonyl as defined above can also be obtained from carboxy and a corresponding alcohol by activation with an appropriate coupling reagent such as benzotriazol-1-yloxytris(dimethylamino)phosphonium hexafluorophosphate (BOP) and a suited base such as 4-dimetylaminopyridine (DMAP) or with an esterification agent such as 3-alkyl-1-p-tolyltriazine or by prior conversion of the carboxyl group into an acid chloride and subsequent treatment with an alcohol. They can also be obtained from carboxy on reaction with a correspondingly substituted alkyl halide in the presence of a base such as potassium carbonate or 1,1,3,3-tetramethylguanidine with, for example, DMF as a solvent.

Alkoxycarbonyl can be reduced with a metal hydride such as $LiAlH_4$ or $NaBH_4$ in the presence of $CaCl_2$ to give hydroxymethyl.

The carboxyl group can be transformed into a group of general formula (Ib), wherein $R^{21}$=—C(O)$NR^aR^b$ on reacting with an amine of formula $NHR^aR^b$ and a suited coupling reagent such as 1,3-dicyclohexylcarbodiimide (DCCI) or BOP. The carboxyl group can also be converted via a Hofman or Schmidt rearrangement to compounds of general formula (Ic) with —Y—$R^{22}$=—NH—$R^{22}$, with $R^{22}$ defined as above and which can be obtained from amino (—Y—$R^{22}$=—$NH_2$) in a manner known per se.

Furthermore, the carboxyl group can be transformed to its next higher homologue by a general sequence of Arndt-Eistert synthesis, which can give compounds with $R^{21}$=hydroxy-lower alkyl after functional group interconversion as described above.

The cyano group of formula (Ia) can be reduced with hydrogen gas and an appropriate transition metal catalyst such as palladium to give, after acetylation or treatment with an alkylsulfonyl chloride, compounds of formula (Ic), wherein $R^{21}$=—$CH_2NHR^c$. Higher homologues with $R^{21}$=—$(CH)_{2-4}NHR^c$ can be obtained from hydroxy-lower alkyl, cited above, by functional group interconversion known per se.

Furthermore, the cyano group can be converted into hydroxyamidino or amidino on treatment with hydroxylamine or ammonia, respectively, under standard conditions.

Compounds where $R^2$ in general formula (I) means heterocyclyl can be obtained:

(i) From above hydroxyamidino by ring-closure with a suited carbon 1 unit such as phosgen or a phosgen substitute, e.g. 1,1'-carbonyldiimidazole, acetic acid or formic acid and/or their corresponding activated forms, such as acetic anhydride, to give optionally substituted (1,2,4)-oxadiazoles in analogy to known procedures.

(ii) From above amidino on reaction with optionally substituted suited carbon 2 building blocks such as optionally substituted chloroacetone or chloroacetaldehyde to give optionally substituted imidazoles.

(iii) From above amidino on reaction with suitably functionalized carbon 3 building blocks such as malonic acid diethyl ester or 3-(dimethylamino)-acryloin or malonaldehyde bis(dimethyl acetale) to give substituted pyrimidine in a manner known per se.

(iv) From above cyano or methoxyimino on condensation with appropriately functionalized carbon 2 building blocks, such as optionally substituted hydroxyacetone or 1-mercapto-2-propanone, to give optionally substituted oxazoles and thiazoles, or alternatively from carbamoyl or thiocarbamoyl and optionally substituted suited carbon 2 building blocks, such as optionally substituted chloroacetone or chloroacetaldehyde, in analogy to standard methods.

Compounds where $R^2$ in general formula (I) means an unsaturated heterocycle such as optionally substituted oxazoline or imidazoline can be prepared from above cyano or alkoxyimino on condensation with optionally substituted ethanolamine or ethylendiamine in analogy to methods described in Tetrahedron Lett. 34 (40) 6395 (1993).

Compounds of general formula (Ic), with Y=—O—, can be obtained from compounds of formula (II) on reaction with a corresponding functionalized alcohol, with tosyl chloride as a reagent, in the presence of a base such as triethyl amine and at elevated temperature, in analogy to a method described in: Zh. Org. Khim., Vol 28, 430 (1991).

The functional groups comprised in the alcohol moiety can be further transformed in a manner known per se.

The employed starting materials, insofar as they are not known or their preparation is described hereinafter, can be prepared in analogy to known processes or processes described below in the examples and summarised in scheme 2.

The central intermediate of general formula (II) can be synthesised from 4-[4,6-dichloro-5-(2-methoxyphenoxy)-pyrimidin-2-yl]-pyridine-1-oxide (described in EP 0 799 209)—according to scheme 2—on reaction with an appropriate sulfonamide of general formula (VI) in a suited solvent such as DMSO or DMF at room temperature or at elevated temperature and in the presence of a suited base such as potassium carbonate, to give the chloro derivatives of general formula (VII).

Scheme 2

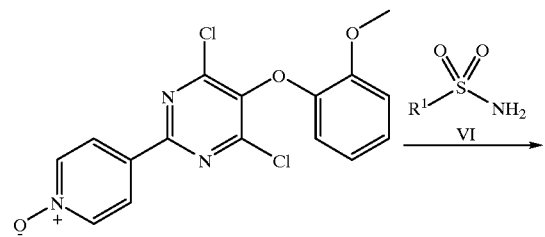

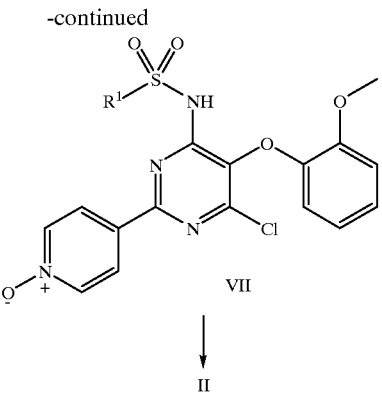

The corresponding sulfonamides can be applied in above reaction in form of their pre-formed sodium or potassium salts. Compounds of formula (VII) can be further transformed by treatment with methanol to give an intermediate of formula (II).

The central intermediate of general formula (III) can be prepared from 5-(2-Methoxy-phenoxy)-2-(pyridin-4-yl) pyrimidine-4,6-diole (EP 0 799 209) by carbamoyl introduction—according to scheme 2a—on reaction with formamide and an oxidizing agent, e.g. hydrogen peroxide, in an aqueous acid solution, e.g. a sulfonic acid solution, in the presence of 15 to 40 mol % iron(II)salts concerning the above mentioned pyridine compound to give a compound of formula (VIII). This compound can be further converted to a compound of formula (IX) on treatment with a water removing and halogenating agent such as $POCl_3$, $PCl_5$ or $SOCl_2$. Introduction of the sulfonamide moiety of general formula (VI) is accomplished as described above.

Scheme 2a

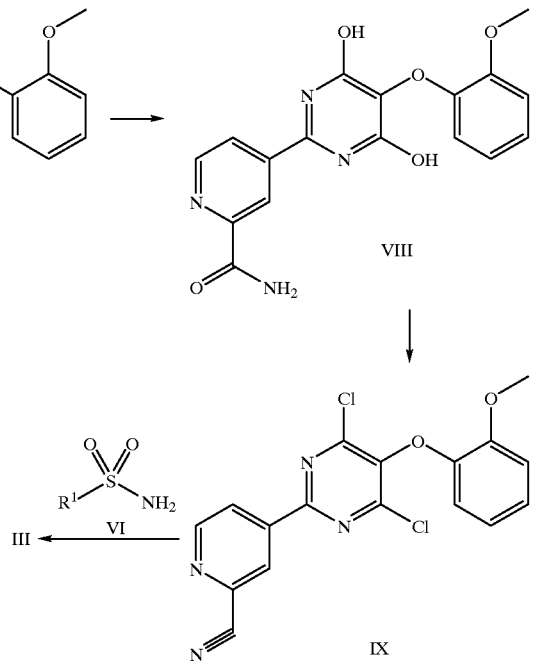

The heterocyclic sulfonamides of general formula (VI) are either already known in the literature, prepared in a manner analogous to established procedures and/or can be derived from corresponding mercapto derivatives in analogy to a known reaction sequence comprising oxidation with $Cl_2$ in an acidic aqueous medium, such as diluted aqueous HCl, to yield the corresponding sulfonyl chlorides which can be transformed with liquid ammonia or aqueous ammonium hydroxide to the sulfonamides. The corresponding sodium or potassium salts can be obtained on treatment with sodium or potassium alkoxide in an appropriate alcohol such as methanol.

b) The compounds of formula (I) with X=—CH— can be prepared as follows and outlined in scheme 3:

formula (Id) where $R^2$ equals —Y—H by alkylation with correspondingly functionalized alkyl halides in the presence of a base such as sodium hydride, in a suited solvent such as DMF or DMSO at room temperature.

Functional groups incorporated in the $R^{22}$ moiety of these compounds can be further transformed by standard procedures, as given below:
(i) Lower alkoxycarbonyl-lower alkyl—as $R^{22}$—into carboxy-lower alkyl, by saponification.
(ii) Lower alkoxycarbonyl-lower alkyl—as $R^{22}$—into hydroxy-lower alkyl, by reduction with a reducing agent such as sodium borohydride in the presence calcium chloride or lithium aluminium hydride.

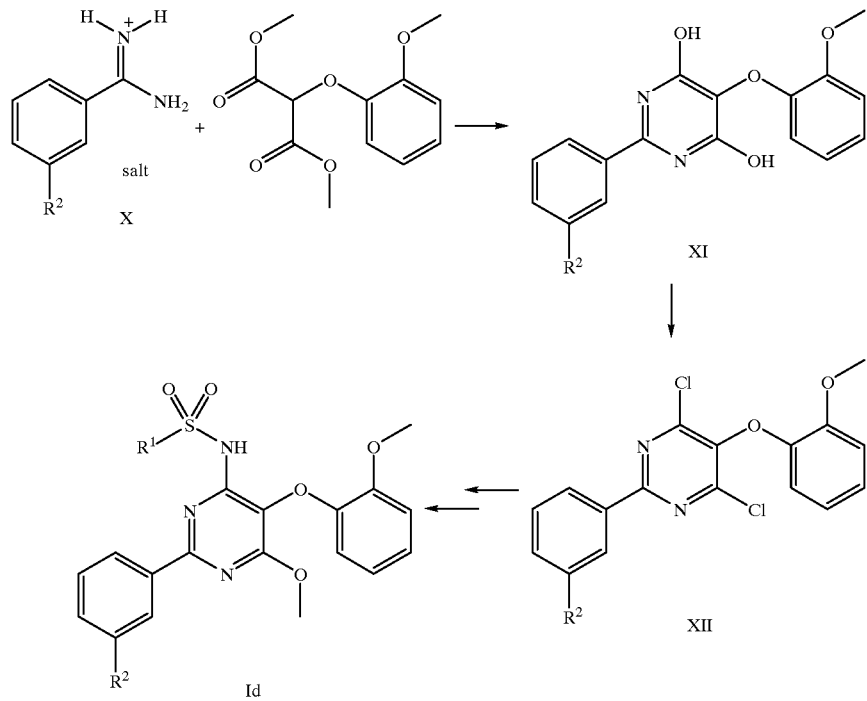

Scheme 3

According to scheme 3, the preparation can be accomplished in analogy to established procedures of pyrimidine synthesis. This comprises:
(i) Reacting appropriately protected or functionalized benzamidines of general formula (X), as their inorganic salts (such as bromide, chloride or tetrafluoroborate) with the diethyl or dimethyl (2-methoxyphenoxy)-malonate to the dihydroxypyrimidines of general formula (XI).
(ii) Conversion to the dichloro derivative with a chlorinating reagent such as $POCl_3$, $PCl_5$ or $SOCl_2$ or with a mixture of both, optionally in the presence of an appropriate base such as triethylamine, to give compounds of general formula (XII).
(iii) Further transformations in analogy to the synthetic steps outlined in scheme 2 to give compounds of general formula (Id).

Compounds of general formula (Id) where $R^2$ equals $R^{21}$ or heterocyclyl can be derived from the corresponding cyano derivatives of general formula (XII) ($R^2$=—CN) by functional group conversions as described in part a).

Compounds of general formula (Id) where $R^2$ equals —Y—$R^{22}$ can be obtained from compounds of general (iii) Carboxy-lower alkyl—as $R^{22}$—into di-lower alkylcarbamoyl-lower alkyl by coupling with a substituted amine and a suited coupling reagent such as DCCI or BOP.

Compounds with $R^2$=—Y—$R^{22}$ and $R^{22}$=lower alkanoyl are prepared from hydroxy or amino—as $R^2$—and a corresponding carboxylic acid, with a coupling reagent such as BOP or DCCI.

Derivatives with $R^{22}$=lower alkoxycarbonyl can be prepared from hydroxy amino—as $R^2$—and an alkylisocyanate or alkoxycarbonyl chlorides.

Alternatively, residue —Y—$R^{22}$ may already be implemented per se or in protected form in formula (X).

Preparation of the starting materials:

The required functionalized benzamidine salts of general formula (X), with the incorporated hydroxyl or amino substituents—as $R^2$—suitably protected as benzyl or allyl or t-butoxyarbonyl or benzyloxycarbonyl, can be obtained:
(i) From the corresponding known arylcarboxamides, in analogy to a method described by Weintraub, J. Org. Chem., 33, 1679 (1968), comprising treatment with trietyloxonium fluroborate to give the corresponding benzimidates fluoroborates salts and subsequent reaction with an excess of ammonia to the corresponding benzamidines as tetrafluorborate salts of general formula (X).

(ii) From substituted benzonitrils by the Pinner reaction to the benzimidate halogenides and subsequent treatment with ammonia to compounds of formula (X) as halogenide salts (chloride or bromide).

The inhibitory activity of the compounds of formula (I) on endothelin receptors can be demonstrated using the test procedures described hereinafter:

I. Inhibition of Endothelin Binding to Recombinant Human $ET_A$ Receptors Expressed in Baculovirus-infected Insect Cells A cDNA coding for human $ET_A$ receptors of human placenta was cloned (M. Adachi, Y.-Y. Yang, Y. Furuichi and C. Miyamoto, BBRC 180, 1265–1272) and expressed in the Baculovirus-insect cell system. Baculovirus-infected insect cells from a 23 l fermenter are centrifuged off (3000×g, 15 minutes, 4° C.) 60 hours after the infection, re-suspended in Tris buffer (5 mM, pH 7.4, 1 mM $MgCl_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenised and centrifuged (25000×g, 15 minutes, 4° C.). After suspension in Tris buffer (75 mM, pH 7.4, 25 mM $MgCl_2$, 250 mM sucrose) 1 ml aliquots (protein content about 3.5 mg/ml) are stored at −85° C.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM $MnCl_2$, 1 mM EDTA and 0.5% bovine serum albumin). 100 μl of this membrane suspension containing 70 μg of protein are incubated with 50 μl of $^{125}$I-endothelin (specific activity 2200 Ci/mMol) in assay buffer (25000 cpm, final concentration 20 pM) and 100 μl of assay buffer containing varying concentrations of test compound. The incubation is carried out at 20° C. for 2 hours or at 4° C. for 24 hours. The separation of free and membrane-bound radio-ligands is carried out by filtration over a glass fibre filter. The inhibitory activity of compounds of formula (I) determined in this test procedure is given in Table 1 as the $IC_{50}$, i.e. as the concentration [nM] which is required to inhibit 50% of the specific binding of $^{125}$I-endothelin.

TABLE 1

| Compound of example | 15 | 22 | 25 | 29 | 32 | 34 | 38 | 48 | 51 | 56 |
|---|---|---|---|---|---|---|---|---|---|---|
| $IC_{50}$ [nM] | ≤50 | ≤50 | ≤50 | ≤50 | ≤50 | ≤50 | ≤50 | ≤50 | ≤50 | ≤50 |

II. Inhibition of Endothelin Binding on Recombinant Human $ET_A$ Receptors, Expressed in CHO Cells Cell culture. CHO cells, expressing recombinant human $ET_A$ receptor are grown in Minimal Essential Alpha Medium (Gibco Laboratories, Paisley, Scotland) supplemented with 0.1 μM methotrexate, 5% dialyzed fetal calf serum, 100 U/ml of penicillin and 100 μg/ml of streptomycin.

Binding assays with whole attached cells are performed in 500 μl Dulbecco's Eagle medium (DMEM) containing 2 mg/ml bovine serum albumin and 25 mM Hepes. After incubation (2 h, 22° C.) in the presence of 35 pM [$^{125}$I]ET-1 and increasing concentrations of various antagonists, the cells are extensively washed and finally solubilized in 1% (w/v) SDS, 0.5 M NaOH and 100 mM EDTA. Each assay is performed three times in triplicates and non specific binding is assessed in the presence of 100 nM unlabelled ET-1. Specific binding is defined as the difference between total binding and non specific binding. $IC_{50}$ values are determined after logit/log transformation of the binding data.

TABLE 2

| Compound of example | 1 | 2 | 7 | 19 | 21 | 23 | 29 | 30 | 36 | 55 |
|---|---|---|---|---|---|---|---|---|---|---|
| $IC_{50}$ [nM] | ≤10 | ≤10 | ≤10 | ≤10 | ≤10 | ≤10 | ≤10 | ≤10 | ≤10 | ≤10 |

III. Inhibition of Endothelin-induced Contractions in Isolated Rat Aorta Rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pre-tension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the EC50 value denoting the endothelin concentration required for a half-maximum contraction.

The corresponding $pA_2$ value, which is a measure of the activity of the test compound, was calculated using a computer programme according to the following equation from the "dose ratio" DR for each individual dosage-activity curve.

$pA_2$ = log(DR-1)-log(antagonist-concentration)

The $EC_{50}$ of endothelin in the absence of test compounds is 0.3 nM.

The $pA_2$ values obtained with compounds of formula (I) are given in the following Table 3.

TABLE 3

| Compound of example | 1 | 7 | 21 | 23 | 35 | 42 | 44 | 52 | 55 | 57 |
|---|---|---|---|---|---|---|---|---|---|---|
| $pA_2$ | ≧8.2 | ≧8.2 | ≧8.2 | ≧8.2 | ≧8.2 | ≧8.2 | ≧8.2 | ≧8.2 | ≧8.2 | ≧8.2 |

IV. Pharmacokinetics of the Endothelin Receptor Antagonists

The pharmacokinetics of the newly synthesised endothelin receptor antagonists were assessed in Wistar rats. The test compounds were dissolved in DMSO at a concentration of 5 mg/mL and administered orally by gavage at a dose of 1 mL/kg body weight corresponding to 5 mg/kg body weight. Two rats were administered per test compound. Blood samples were collected from the retro-orbital sinus at 1 and 5 h post dose in one rat, and at 3 and 7 h post dose in the other rat. In addition a terminal 24 h blood sample was collected from both rats by heart puncture. Blood was collected on EDTA-NaF. Plasma was derived by centrifugation at 2000 g at +4° C. for 15 min. Plasma samples were assayed for active drug related material with a bioassay, based on the binding competition of tested compounds and $^{125}$I ET-1 on recombinant $ET_A$ receptors. Quantitation of plasma samples was by comparison to a calibration curve build up from control rat plasma spiked with known concentrations of the test compounds. Selected findings are summarised in the following table:

TABLE 4

| Test compound of example | Peak concentration in rat plasma (ng/mL) | Area under the plasma concentration time curve (ng.h/mL) |
|---|---|---|
| 7 | ≧1,500 | ≧10,000 |
| 22 | ≧1,500 | ≧10,000 |
| 19 | ≧1,500 | ≧10,000 |
| 52 | ≧1,500 | ≧10,000 |
| 35 | ≧1,500 | ≧10,000 |
| 42 | ≧1,500 | ≧10,000 |

On the basis of their capability of inhibiting endogenous endothelin binding, the compounds of formula (I) can be used as medicaments for the treatment of disorders which are associated with abnormal vascular tone and endothelial dysfunction.

Therefore, the application field of the compounds of formula (I) could be heart failure (acute and chronic), systemic and pulmonary hypertension, acute ischaemic coronary syndrome, angina pectoris, renal failure (acute and chronic), organ transplant (e.g. liver, heart, kidney), cyclosporin nephrotoxicity, vasospastic disease (subarachnoid haemorrhage but also haemorrhagic and non-haemorrhagic stroke, Raynaud syndrome), peripheral artery occlusive disease, prevention of restenosis after stent or balloon angioplasty, septic shock or multiple organ failure as that occurring in intensive care, asthma, chronic obstructive pulmonary disease, gastric and duodenal ulcus, liver cirrhosis, pancreatitis (acute and chronic), inflammatory bowel disease, fibrosis, artheriosclerosis, obesity, glaucoma, prostatic adenoma, migraine, erectile dysfunction, adjunct to cancer therapy as well as other disorders associated with endothelin activities.

The compounds of formula (I) can also be administered in combination with antihypertensive drugs, antiarrhythmics, anti angina, antithrombotic and lipid lowering agents as well as antioxidants.

It will be appreciated that the compounds of general formula (I) in this invention may be derivatised at functional groups to provide prodrug derivatives which are capable of conversion back to the parent compounds in vivo. Examples of such prodrugs include the physiologically acceptable and metabolically labile ester derivatives, such as acetoxymethyl esters, acetoxyethyl esters, lower alkylcarbonyloxymethyl esters, lower alkoxycarbonyloxyethyl esters, cycloalkyloxycarbonyloxymethyl esters, cycloalkyloxycarbonyloxyethyl esters, lower alkylcarbonylmethyl esters, lower alkylcarbonylethyl esters, benzoylmethyl esters, benzoylethyl esters, hydroxy-lower alkylcarbonylmethyl esters, hydroxy-lower alkylcarbonylethyl esters, 5-methyl-2-oxo-[1,3]dioxol-4-ylmethyl esters, 5-methyl-2-oxo-[1,3]dioxol-4-ylethyl esters, methoxymethyl esters, methylthiomethyl esters, pivaloyloxymethyl esters and the like. Preferable prodrug esters are for example 1-acetoxy-ethyl esters, 2,2-dimethyl-propionyloxymethyl esters, 1-ethoxycarbonyloxy-ethyl esters, 1-cyclohexyloxy-carbonyloxy-ethyl esters, 2-oxo-propyl esters, 3,3-dimethyl-2-oxo-butyl esters, 2-oxo-2-phenyl-ethyl esters, 4-methyl-2-oxo-pentyl esters, 3-hydroxy-2-oxo-propyl esters and 5-methyl-2-oxo-[1,3]dioxol-4-ylmethyl esters. For example, preferable prodrugs of 4-[4-methoxy-5-(2-methoxy-phenoxy)-6-(5-methyl-pyridine-2-sulfonylamino)-pyrimidin-2-yl]-pyridine-2-carboxylic acid include 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester, 4-[4-methoxy-5-(2-methoxy-phenoxy)-6-(5-methyl-pyridine-2-sulfonylamino)-pyrimidin-2-yl]-pyridine-2-carboxylic acid 2,2-dimethyl-propionyloxymethyl ester, 4-[4-methoxy-5-(2-methoxy-phenoxy)-6-(5-methyl-pyridine-2-sulfonylamino)-pyrimidin-2-yl]-pyridine-2-carboxylic acid 1-ethoxycarbonyloxy-ethyl ester, 4-[4-methoxy-5-(2-methoxy-phenoxy)-6-(5-methyl-pyridine-2-sulfonylamino)-pyrimidin-2-yl]-pyridine-2-carboxylic acid 1-cyclohexyloxycarbonyloxy-ethyl ester, 4-[4-methoxy-5-(2-methoxy-phenoxy)-6-(5-methyl-pyridine-2-sulfonylamino)-pyrimidin-2-yl]-pyridine-2-carboxylic acid 2-oxo-propyl ester, 4-[4-methoxy-5-(2-methoxy-phenoxy)-6-(5-methyl-pyridine-2-sulfonylamino)-pyrimidin-2-yl]-pyridine-2-carboxylic acid 3,3-dimethyl-2-oxo-butyl ester, 4-[4-methoxy-5-(2-methoxy-phenoxy)-6-(5-methyl-pyridine-2-sulfonylamino)-pyrimidin-2-yl]-pyridine-2-carboxylic acid 2-oxo-2-phenyl-ethyl ester, 4-[4-methoxy-5-(2-methoxy-phenoxy)-6-(5-methyl-pyridine-2-sulfonylamino)-pyrimidin-2-yl]-pyridine-2-carboxylic acid 4-methyl-2-oxo-pentyl ester, 4-[4-methoxy-5-(2-methoxy-phenoxy)-6-(5-methyl-pyridine-2-sulfonylamino)-pyrimidin-2-yl]-pyridine-2-carboxylic acid 3-hydroxy-2-oxo-propyl ester, 4-[4-methoxy-5-(2-methoxy-phenoxy)-6-(5-methyl-pyridine-2-sulfonylamino)-pyrimidin-2-yl]-pyridine-2-carboxylic acid 5-methyl-2-oxo-[1,3]dioxol-4-ylmethyl ester, and the like; most preferable prodrug is 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

Additionally, any physiologically acceptable equivalents of the compounds of general formula (I), similar to the metabolically labile esters, which are capable of producing the parent compounds of general formula (I) in vivo, are within the scope of this invention.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g. intravenously, intramuscularly, subcutaneously, intrathecally or transdermally, using for example injectable solutions. Furthermore, administration can be carried out sublingually or as opthalmological preparations or as an aerosol, for example in the form of a spray.

For the preparation of tablets, coated tablets, dragées or hard gelatine capsules the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which may be used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. Most preferred form of use is oral administration. The dosages in which the compounds of formula (I) are administered in effective amounts depend on the nature of the specific active ingredient, the age and the requirements of the patient and the mode of application. In general, dosages of about 0.01–10 mg/kg body weight per day come into consideration.

The following Examples shall illustrate preferred embodiments of the present invention but are not intended to limit the scope of the invention. Of the abbreviations used therein, DMSO signifies dimethylsulfoxide, DMF signifies dimethylformamide, THF signifies tetrahydrofuran, EtOAc denotes ethyl acetate, TLC signifies thin layer chromatography, RT signifies room temperature, HPLC signifies high performance liquid chromatography, ISP signifies Ion Spray Mass Spectrometry—positive mode, ISN signifies Ion Spray Mass Spectrometry— negative mode, EI signifies Electron Impact Mass Spectrometry, mp signifies melting point and M signifies molecular mass.

Example 1 a) 1.46 g of 5-methyl-pyridine-2-sulfonic acid [2-(3-benzyloxy-phenyl)-6-methoxy-5-(2-methoxy-phenoxy)-pyrimidin-4-yl]-amide were dissolved in dioxane (25 ml) by gentle warming than ethanol (50 ml) was added followed by cyclohexadiene (6 g) and palladium on charcoal, 10%, (1.46 g). The solution was refluxed for 20 h, the catalyst removed by filtration and the solution concentrated on a rotary evaporator. The yellow crystalline solid that precipitated was collected, washed with ether and dried in a vacuum to give the desired 5-methyl-pyridine-2-sulfonic acid [2-(3-hydroxy-phenyl)-6-methoxy-5-(2-methoxy-phenoxy)-pyrimidin-4-yl]-amide as off-white crystals. ISP mass spectrum, m/e 495.2 (M+1 calculated for $C_{24}H_{22}N_4O_6S_1$: 495). Melting point 211°–216° C.

Preparation of the starting material:

b) To a solution of 13.7 g of 3-hydroxybenzamide and 25.6 of benzyl bromide in acetone (400 ml) were added 25.6 g of potassium carbonate at RT. The mixture was then refluxed for 6 h after which time the reaction was completed according to TLC analysis ($CH_2Cl_2$/MeOH: 20/1). The reaction mixture was cooled to RT and partitioned between EtOAc and water, the organic layer was separated, dried over sodium sulphate and concentrated in vacuo. The crystalline residue obtained was suspended in n-hexane (200 ml), the crystals were filtered off under suction and dried in a vacuum to give 3-benzyloxy-benzamide as a white crystalline solid, mp 136°–140° C.

c) Under an atmosphere of argon 11.36 g of 3-benzyloxybenzamide were suspended in $CH_2Cl_2$ (200 ml) and 9.5 g triethyloxonium fluoroborate in $CH_2Cl_2$ (100 ml) were added dropwise on ice cooling. The reaction mixture was then stirred further 20 h at RT until completion of reaction according to TLC analysis ($CH_2Cl_2$/MeOH: 15/1). The solid which had formed was filtered off, washed with ether to give the desired ethyl m-benzyloxybenzimidate tetrafluoroborate as white crystals, mp 152°–154° C., which was used without further purification in the next step.

d) A suspension of 8.57 g of ethyl m-benzyloxybenzimidate tetrafluoroborate in ethanol (120 ml) was cooled to −70° C. and then treated with liquid ammonia (100 ml). The cooling bath was removed and the reaction mixture stirred for 69 h until the reaction was complete (TLC analysis). The solvent was removed in vacuo to give the desired m-benzyloxybenzamidine tetrafluoroborate as a white solid, mp 125°–127° C., that was essentially pure and used without further purification in the next step.

e) 6.3 g of dimethyl (2-methoxyphenoxy)malonate were added dropwise within 5 minutes under an argon atmosphere to a solution of 1.72 g of sodium in methanol (150 ml) at 5° C. Stirring was continued for 30 minutes (5° C.) then 7.85 g of m-benzyloxy-benzamidine tetrafluoroborate in methanol (50 ml) were added within 5 minutes at 5° C. and the mixture was then stirred for further 20 h at RT. The solvent was removed in vacuo and the residue partitioned between water and EtOAc (each 50 ml). The cold aqueous phase was acidified dropwise with conc. HCl the precipitate filtered off under suction, washed with water and dried under reduced pressure to give the desired 2-(3-benzyloxy-phenyl)-5-(2-methoxy-phenoxy)-pyrimidine-4,6-diol as an off-white solid, mp 192°–195° C.

Further product was obtained by washing the EtOAc phase with 3N HCl, drying of the organic layer over $Na_2SO_4$ and subsequent removal of the solvent under vacuo.

f) To a suspension of 4.16 g of 2-(3-benzyloxy-phenyl)-5-(2-methoxy-phenoxy)-pyrimidine-4,6-diol in $POCl_3$(18.2 ml) were added at RT 4.58 g of $PCl_5$ followed by 5.1 ml of N-ethyldiisopropylamine and 3.31 g of tetraetylammonium chloride. The mixture was then heated to reflux for 30 h. The deep-brown mixture was cooled to RT, poured on ice and extracted with ether. The organic layer was washed with water, treated with charcoal and dried over $Mg_2SO_4$. The solvent was removed in vacuo, the residue was applied to a short silica gel column (120 g) with ether as eluent. Combination of the purified fractions and concentration in vacuo gave the desired 2-(3-benzyloxy-phenyl)-4,6-dichloro-5-(2-methoxy-phenoxy)-pyrimidine as a light-brown crystalline solid, mp 127°–132° C.

g) 4.53 g of 2-(3-benzyloxy-phenyl)-4,6-dichloro-5-(2-methoxy-phenoxy)-pyrimidine and 4.2 g of 5-methylpyridyl-2-sulfonamide potassium salt (preparation described in EP 713'875 and Bioorg. Med. Chem. Lett., 1997, 7, 2223–2228) were dissolved in DMSO (120 ml) and the solution was stirred for 12 h at RT. It was then partitioned between EtOAc and 1N HCl, the organic layer was washed with water dried over $Na_2SO_4$ and the solvent was removed in vacuo. The solid residue was triturated with ether and filtered off by suction to give 5-methyl-pyridine-2-sulfonic acid [2-(3-benzyloxy-phenyl)-6-chloro-5-(2-methoxy-phenoxy)-pyrimidin-4-yl]-amide as light-brown crystals, mp 176°–180° C.

h) To a solution of 0.92 g sodium in MeOH (75 ml) were added 2.35 g of 5-methyl-pyridine-2-sulfonic acid[2-(3-benzyloxy-phenyl)-6-chloro-5-(2-methoxy-phenoxy)-pyrimidin-4-yl]-amide at RT and the mixture was then refluxed for 20 h until completion of the reaction (according to TLC analysis). The mixture was then poured on cold 1N HCL and the product extracted into EtOAc. The organic layer was dried over $Na_2SO_4$ and the solvent removed in vacuo. The solid residue was triturated with ether and filtered off by suction to 5-methyl-pyridine-2-sulfonic acid [2-(3-benzyloxy-phenyl)-6-methoxy-5-(2-methoxy-phenoxy)-pyrimidin-4-yl]-amide as off-white crystals, mp 180°–183° C.

Example 2

0.41 g of 5-methyl-pyridine-2-sulfonic acid [2-(3-hydroxy-phenyl)-6-methoxy-5-(2-methoxy-phenoxy)-pyrimidin-4-yl]-amide, product of example 1, were dissolved in DMF (30 ml) and treated with NaH (0.061 g of a 65% NaH suspension in oil) under ice cooling. The mixture was stirred for 1 h at RT, treated dropwise with 0.11 g of methyl chloroacetate and was stirred at RT for 20 h until the reaction was completed according to TLC analysis ($CH_2Cl_2$/EtOAc: 4/1). The mixture was partitioned between brine and EtOAc the organic layer was dried over $Na_2SO_4$ and the solvent removed in vacuo. The residue was purified on a silica gel chromatography column (eluted with $Me_2Cl_2$/EtOAc: 7/1). Combination of the purified fractions and evacuation in vacuo afforded {3-[4-methoxy-5-(2-methoxy-phenoxy)-6-(5-methyl-pyridine-2-sulfonylamino)-pyrimidin-2-yl]-phenoxy}-acetic acid methyl ester as a light yellow crystalline solid. ISP mass spectrum, m/e 567.2 (M+1 calculated for $C_{27}H_{26}N_4O_8S$: 567).

Example 3

In analogy to example 2, from 5-methyl-pyridine-2-sulfonic acid [2-(3-hydroxy-phenyl)-6-methoxy-5-(2-methoxy-phenoxy)-pyrimidin-4-yl]-amide and ethyl chloroacetate there was obtained {3-[4-methoxy-5-(2-methoxy-phenoxy)-6-(5-methyl-pyridine-2-sulfonylamino)-pyrimidin-2-yl]-phenoxy}-acetic acid ethyl ester as a white solid. ISP mass spectrum, m/e 581.1 (M+1 calculated for $C_{28}H_{28}N_4O_8S$: 581).

Example 4

In analogy to example 2, from 5-methyl-pyridine-2-sulfonic acid [2-(3-hydroxy-phenyl)-6-methoxy-5-(2-methoxy-phenoxy)-pyrimidin-4-yl]-amide and 2-chloroacetamide there was obtained 2-{3-[4-methoxy-5-(2-methoxy-phenoxy)-6-(5-methyl-pyridine-2-sulfonylamino)-pyrimidin-2-yl]-phenoxy}-acetamide as a white solid. ISP mass spectrum, m/e 552.1 (M+1 calculated for $C_{26}H_{25}N_5O_7S$: 552).

Example 5

In analogy to example 2, from 5-methyl-pyridine-2-sulfonic acid [2-(3-hydroxy-phenyl)-6-methoxy-5-(2-methoxy-phenoxy)-pyrimidin-4-yl]-amide and 2-chloro-N,N-dimethylacetamide there was obtained 2-{3-[4-methoxy-5-(2-methoxy-phenoxy)-6-(5-methyl-pyridine-2-sulfonylamino)-pyrimidin-2-yl]-phenoxy}-N,N-dimethyl-acetamide as a white solid. ISP mass spectrum, m/e 580.1 (M+1 calculated for $C_{28}H_{29}N_5O_7S$: 580).

Example 6

85 mg of {3-[4-methoxy-5-(2-methoxy-phenoxy)-6-(5-methyl-pyridine-2-sulfonylamino)-pyrimidin-2-yl]-phenoxy}-acetic acid methyl ester, product of example 2, dissolved in MeOH (30 ml) were treated at RT with 1N NaOH (0.9 ml) and the solution was stirred for 1 h until the transformation was complete according to TLC analysis ($CH_2Cl_2$/EtOAc: 3:1). The reaction mixture was partitioned between 1N HCl and $CH_2Cl_2$, the organic layer was dried over $Na_2SO_4$ and the solvent removed in vacuo. The residue upon triturating with ether provided the desired {3-[4-methoxy-5-(2-methoxy-phenoxy)-6-(5-methyl-pyridine-2-sulfonylamino)-pyrimidin-2-yl]-phenoxy}-acetic acid as a white solid. ISN mass spectrum, m/e 551 (M−1 calculated for $C_{26}H_{24}N_4O_8S$: 551).

Example 7

70 mg of {3-[4-methoxy-5-(2-methoxy-phenoxy)-6-(5-methyl-pyridine-2-sulfonylamino)-pyrimidin-2-yl]-phenoxy}-acetic acid methyl ester, product of example 2, were dissolved in a mixture of EtOH/THF (each 3 ml) on gentle warming and subsequently treated with 27.4 mg of $CaCl_2$ and 18.7 mg of $NaBH_4$ at RT. The reaction mixture was stirred at RT for 1.5 h until which time starting material was consumed according to TLC analysis ($CH_2Cl_2$/EtOAc: 3/1). The mixture was partitioned between 10% citric acid and EtOAc. The organic layer was dried over $Na_2SO_4$ and the solvent removed in vacuo. The residue was purified on a silica gel chromatography column (eluted with $Me_2Cl_2$EtOAc: 3/1). Combination of the purified fractions and evacuation in vacuo afforded 5-methyl-pyridine-2-sulfonic acid [2-[3-(2-hydroxy-ethoxy)-phenyl]-6-methoxy-5-(2-methoxy-phenoxy)-pyrimidin-4-yl]-amide as a white solid. ISP mass spectrum, m/e 539.3 (M+1 calculated for $C_{26}H_{26}N_4O_7S$: 539).

Example 8

49.5 mg of 5-methyl-pyridine-2-sulfonic acid [2-(3-hydroxy-phenyl)-6-methoxy-5-(2-methoxy-phenoxy)- pyrimidin-4-yl]-amide, product of example 1, dissolved in acetontrile (3 ml) was treated at RT subsequently with 25.8 mg of n-ethyldiisopropylamine, 53 mg of benzotriazol-1-yloxytris-(dimethylamino)-phosphonium hexafluorophosphate and, 0.5 h later, with 72 mg of acetic acid. The mixture was stirred for 12 h, partitioned between water and EtOAc. The organic layer was dried over $Na_2SO_4$ and the solvent removed in vacuo. The residue was purified on a silica gel chromatography column (eluted with $Me_2Cl_2$/EtOAc: 8/1). Combination of the purified fractions and evacuation in vacuo afforded acetic acid 3-[4-methoxy-5-(2-methoxy-phenoxy)-6-(5-methyl-pyridine-2-sulfonylamino)-pyrimidin-2-yl]-phenyl ester as a white solid. ISP mass spectrum, m/e 537.2 (M+1 calculated for $C_{26}H_{24}N_4O_7S$: 537).

Example 9 a) A solution of 0.35 g of 5-methyl-thiazole-2-sulfonic acid [2-(3-benzyloxy-phenyl)-6-methoxy-5-(2-methoxy-phenoxy)-pyrimidin-4-yl]-amide dissolved in $CH_2Cl_2$ (40 ml) is cooled to 0° C. and treated dropwise with 4.8 ml of a 1M solution of $TiCl_4$ in $CH_2Cl_2$. The orange solution is stirred at 0° C. for 0.5 h until the starting material was consumed according to TLC analysis ($Me_2Cl_2$/EtOAc: 4/1). The reaction solution was then poured on ice, the product extracted into $Me_2Cl_2$ the organic layer dried over $Na_2SO_4$ and the solvent removed in vacuo. The residue was washed with ether/hexane to give 5-methyl-thiazole-2-sulfonic acid [2-(3-hydroxy-phenyl)-6-methoxy-5-(2-methoxy-phenoxy)-pyrimidin-4-yl]-amide as an off-white crystalline solid. ISN mass spectrum, m/e 499.1 (M−1 calculated for $C_{22}H_{20}N_4O_6S_2$: 499).

Preparation of the starting material:

b) 2.23 g of 5-methylene-thiazolidine-2-thione (preparation described in: Liebigs Ann. Chem., 1985, 58–64) were dissolved in 36% aqueous HCl (150 ml), cooled to −20° C. and $Cl_2$ was bubbled through the solution for 0.5 h while keeping its temperature below −20° C. Ether (400 ml cooled to −15° C.) was then added and after stirring for 5 minutes the layers were separated. The organic layer was treated with liquid $NH_3$ (200 ml) and the mixture allowed warming slowly to RT. The solvent was removed in vacuo to give 5-Methyl-thiazole-2-sulfonic acid amide as an off-white solid. EI mass spectrum, m/e 178 (M calculated for $C_4H_6N_2O_2S_2$: 178).

The corresponding potassium salt was prepared from the sulfonamide on treatment with potassium t-butylate in MeOH.

c) In analogy to example 1g), from 5-methyl-thiazole-2-sulfonic acid amide potassium salt and 2-(3-benzyloxy-phenyl)-4,6-dichloro-5-(2-methoxy-phenoxy)-pyrimidine, product of example 1f), there was obtained 5-methyl-thiazole-2-sulfonic acid [2-(3-benzyloxy-phenyl)-6-chloro-5-(2-methoxy-phenoxy)-pyrimidin-4-yl]-amide as an off-white solid. ISN mass spectrum, m/e 593 (M−1 calculated for $C_{28}H_{23}ClN_4O_5S_2$: 593).

d) Analogously to example 1h), by treatment of 5-methyl-thiazole-2-sulfonic acid [2-(3-benzyloxy-phenyl)-6-chloro-5-(2-methoxy-phenoxy)-pyrimidin-4-yl]-amide with $NaOCH_3$ in MeOH there was obtained 5-methyl-thiazole-2-sulfonic acid [2-(3-benzyloxy-phenyl)-6-methoxy-5-(2-methoxy-phenoxy)-pyrimidin-4-yl]-amide as an off-white solid. ISP mass spectrum, m/e 591.1 (M+1 calculated for $C_{29}H_{26}N_4O_6S_2$: 591).

Example 10

In analogy to example 2, from 5-methyl-thiazole-2-sulfonic acid [2-(3-hydroxy-phenyl)-6-methoxy-5-(2-methoxy-phenoxy)-pyrimidin-4-yl]-amide, product of example 9, and methyl chloroacetate there was obtained {3-[4-Methoxy-5-(2-methoxy-phenoxy)-6-(5-methyl-thiazole-2-sulfonylamino)-pyrimidin-2-yl]-phenoxy}-acetic acid methyl ester as a white solid. ISN mass spectrum, m/e 571 (M−1 calculated for $C_{25}H_{24}N_4O_8S_2$: 571).

Example 11

Analogously to example 6, by saponification of {3-[4-methoxy-5-(2-methoxy-phenoxy)-6-(5-methyl-thiazole-2-sulfonylamino)-pyrimidin-2-yl]-phenoxy}-acetic acid methyl ester, product of example 10, with 1N aqueous NaOH in MeOH there was obtained {3-[4-methoxy-5-(2-methoxy-phenoxy)-6-(5-methyl-thiazole-2-sulfonylamino)-pyrimidin-2-yl]-phenoxy}-acetic acid as a white solid. ISN mass spectrum, m/e 557 (M−1 calculated for $C_{24}H_{22}N_4O_6S_2$: 557).

Example 12

In analogy to example 7, by reduction of {3-[4-methoxy-5-(2-methoxy-phenoxy)-6-(5-methyl-thiazole-2-sulfonylamino)-pyrimidin-2-yl]-phenoxy}-acetic acid methyl ester, product of example 10, with $NaBH_4/CaCl_2$ there was obtained 5-methyl-thiazole-2-sulfonic acid [2-[3-(2-hydroxy-ethoxy)-phenyl]-6-methoxy-5-(2-methoxy-phenoxy)-pyrimidin-4-yl]-amide as a white solid. ISN mass spectrum, m/e 543.1 (M−1 calculated for $C_{24}H_{22}N_4O_7S_2$: 543).

Example 13 a) In analogy to example 1a), by benzyl ether cleavage under hydrogen transfer conditions of 5-hydroxymethyl-pyridine-2-sulfonic acid [2-(3-benzyloxy-phenyl)-6-methoxy-5-(2-methoxy-phenoxy)-pyrimidin-4-yl]-amide with cyclohexadiene and palladium on charcoal there was obtained 5-hydroxymethyl-pyridine-2-sulfonic acid [2-(3-hydroxy-phenyl)-6-methoxy-5-(2-methoxy-phenoxy)-pyrimidin-4-yl]-amide as a light yellow solid. ISN mass spectrum, m/e 509.2 (M−1 calculated for $C_{24}H_{22}N_4O_7S$: 509).

Preparation of the starting material:

b) 5.1 g of 5-methypyridyl-2-sulfonamide in water (100 ml), were treated with 60 ml of 1N NaOH and 9.48 g of $KMnO_4$ and the mixture was refluxed for 2.5 h. The reaction mixture was cooled to RT, and filtered. The filtrate was washed with AcOEt, the pH of the water layer was adjusted to pH=1 with $KHSO_4$, NaCl was added and the product was extracted into AcOEt. The organic layer was dried over $NaSO_4$ and the solvent removed in vacuo to give the desired 5-carboxypyridyl-2-sulfonamide as a white solid. ISN mass spectrum, m/e 201.1 (M−1 calculated for $C_6H_6N_2O_4S$: 201).

c) To a solution of 2.02 g of 5-carboxypyridyl-2-sulfonamide in THF (100 ml) were added 1.49 g of 3-methyl-1-p-tolyltriazene and the solution was stirred a RT until the starting material was consumed according to TLC analysis ($CH_2Cl_2$/MeOH: 30/1). The reaction solution was concentrated in vacuo, the precipitated crystalline solid triturated with ether, filtered off by suction and dried in a vacuum to give 5-methoxycarbocarbonylpyridyl-2-sulfonamide as a crystalline off-white solid. ISN mass spectrum, m/e 215.2 (M−1 calculated for $C_7H_8N_2O_4S$: 215).

d) 0.4 g of 5-methoxycarbocarbonylpyridyl-2-sulfonamide in THF (20 ml) were added dropwise to a slurry of $LiAlH_4$ in a mixture THF/ether (each 10 ml) at −10° C. The mixture was stirred 10 minutes at RT, cooled to −5° C.

The reaction was then quenched by adding EtOAc (5 ml) followed by 10% aqueous citric acid (20 ml). The product was extracted into ether which was dried and gave after evaporation of the solvent 5-hydroxymethyl-pyridyl-2-sulfonamide. ISN mass spectrum, m/e 187.1 (M−1 calculated for $C_6H_8N_2O_3S$: 218). It was used in the subsequent reaction without further purification.

e) In analogy to example 1g), from 5-hydroxymethyl-pyridyl-2-sulfonamide and 2-(3-benzyloxy-phenyl)-4,6-dichloro-5-(2-methoxy-phenoxy)-pyrimidine, product of example 1f), there was obtained 5-hydroxymethyl-pyridine-2-sulfonic acid [2-(3-benzyloxy-phenyl)-6-chloro-5-(2-methoxy-phenoxy)-pyrimidin-4-yl]-amide as an off-white amorphous solid. ISN mass spectrum, m/e 603 (M−1 calculated for $C_{30}H_{25}ClN_4O_6S$: 603).

f) Analogously to example 1h), by treatment of 5-hydroxymethyl-pyridine-2-sulfonic acid [2-(3-benzyloxy-phenyl)-6-chloro-5-(2-methoxy-phenoxy)-pyrimidin-4-yl]-amide with $NaOCH_3$ in MeOH there was obtained 5-hydroxymethyl-pyridine-2-sulfonic acid [2-(3-benzyloxy-phenyl)-6-methoxy-5-(2-methoxy-phenoxy)-pyrimidin-4-yl]-amide as an off-white solid. ISN mass spectrum, m/e 599 (M−1 calculated for $C_{31}H_{28}N_4O_7S$: 599).

Example 14 a) In analogy to example 1a), by benzyl ether cleavage under hydrogen transfer conditions of 5-(1-hydroxy-1-methyl-ethyl)-pyridine-2-sulfonic acid [2-(3-benzyloxy-phenyl)-6-methoxy-5-(2-methoxy-phenoxy)-pyrimidin-4-yl]-amide with cyclohexadiene and palladium on charcoal there was obtained 5-(1-hydroxy-1-methyl-ethyl)-pyridine-2-sulfonic acid [2-(3-hydroxy-phenyl)-6-methoxy-5-(2-methoxy-phenoxy)-pyrimidin-4-yl]-amide as a white solid. ISP mass spectrum, m/e 539.3 (M+1 calculated for: $C_{26}H_{26}N_4O_7S$ 539).

Preparation of the starting material:

b) To a solution of 5-isopropyl-pyridine-2-sulfonamide potassium salt (synthesis described in EP 0 799 209) in water (10 ml) were added 1.2 g of $KMnO_4$ at RT and the mixture was then refluxed for 30 minutes. The mixture was cooled to RT, acidified with diluted HCl and the product was extracted into AcOEt. The organic layer was washed with washed with water, dried over $Na_2SO_4$ and concentrated in vacuo to give (5-(1-hydroxy-1-methyl-ethyl))-pyridine-2-sulfonic acid amide as yellow oil. EI mass spectrum, m/e 216 (M calculated for: $C_8H_{12}N_2O_3S$ 216).

The material was used without further purification. The corresponding potassium salt was prepared from the sulfonamide on treatment with potassium t-butylate in MeOH.

c) In analogy to example 1g), from 5-(1-hydroxy-1-methyl-ethyl)-pyridine-2-sulfonic acid amide potassium salt and 2-(3-Benzyloxy-phenyl)-4,6-dichloro-5-(2-methoxy-phenoxy)-pyrimidine, product of example 1f), there was obtained 5-(1-hydroxy-1-methyl-ethyl)-pyridine-2-sulfonic acid [2-(3-benzyloxy-phenyl)-6-chloro-5-(2-methoxy-phenoxy)-pyrimidin-4-yl]-amide as an off-white solid. ISP mass spectrum, m/e 633.1 (M+1 calculated for $C_{32}H_{29}ClN_4O_6S$: 633).

d) Analogously to example 1h), by treatment of 5-(1-hydroxy-1-methyl-ethyl)-pyridine-2-sulfonic acid [2-(3-benzyloxy-phenyl)-6-chloro-5-(2-methoxy-phenoxy)-pyrimidin-4-yl]-amide with $NaOCH_3$ in MeOH there was obtained 5-(1-hydroxy-1-methyl-ethyl)-pyridine-2-sulfonic acid [2-(3-benzyloxy-phenyl)-6-methoxy-5-(2-methoxy-phenoxy)-pyrimidin-4-yl]-amide as an off-white solid. ISP mass spectrum, m/e 629.1 (M+1 calculated for $C_{33}H_{32}N_4O_7S$: 629).

Example 15 a) In analogy to example 9a), by benzyl ether cleavage of 5-isopropenyl-pyridine-2-sulfonic acid [2-(3-benzyloxy-phenyl)-6-methoxy-5-(2-methoxy-phenoxy)-pyrimidin-4-yl]-amide with $TiCl_4$ in $CH_2Cl_2$ there was obtained 5-isopropenyl-pyridine-2-sulfonic acid [2-(3-hydroxy-phenyl)-6-methoxy-5-(2-methoxy-phenoxy)-pyrimidin-4-yl]-amide as a white solid. ISN mass spectrum, m/e 519.1 (M+1 calculated for $C_{26}H_{24}N_4O_6S$: 519).

Preparation of the starting material:

b) A solution of 0.1 g of (5-(1-hydroxy-1-methyl-ethyl))-pyridine-2-sulfonic acid amide, product of example 14 b), in $CF_3CO_2H$ (2 ml) was refluxed for 20 h. The solvent was then removed in vacuo to give 5-isopropenyl-pyridine-2-sulfonic acid amide as a white solid which was essentially pure. EI mass spectrum, m/e 198 (M calculated for $C_8H_{10}N_2O_2S$: 198).

The corresponding potassium salt was prepared from the sulfonamide on treatment with potassium t-butylate in MeOH.

c) In analogy to example 1g), from 5-isopropenyl-pyridine-2-sulfonic acid amide potassium salt and 2-(3-benzyloxy-phenyl)-4,6-dichloro-5-(2-methoxy-phenoxy)-pyrimidine, product of example 1f), there was obtained 5-isopropenyl-pyridine-2-sulfonic acid [2-(3-benzyloxy-phenyl)-6-chloro-5-(2-methoxy-phenoxy)-pyrimidin-4-yl]-amide as an off-white solid. ISP mass spectrum, m/e 613.1 (M−1 calculated for $C_{32}H_{27}ClN_4O_5S$: 613+).

d) Analogously to example 1h), by treatment of 5-isopropenyl-pyridine-2-sulfonic acid [2-(3-benzyloxy-phenyl)-6-chloro-5-(2-methoxy-phenoxy)-pyrimidin-4-yl]-amide with $NaOCH_3$ in MeOH there was obtained 5-isopropenyl-pyridine-2-sulfonic acid [2-(3-benzyloxy-phenyl)-6-methoxy-5-(2-methoxy-phenoxy)-pyrimidin-4-yl]-amide as white solid. ISN mass spectrum, m/e 609.1 (M−1 calculated for $C_{33}H_{30}N_4O_6S$: 609).

Example 16

In analogue to example 2, from 5-isopropenyl-pyridine-2-sulfonic acid [2-(3-hydroxy-phenyl)-6-methoxy-5-(2-methoxy-phenoxy)-pyrimidin-4-yl]-amide, product of example 15, and ethyl chloroacetate there was obtained {3-[4-(5-isopropenyl-pyridine-2-sulfonylamino)-6-methoxy-5-(2-methoxy-phenoxy)-pyrimidin-2-yl]-phenoxy}-acetic acid ethyl ester as an off-white solid. ISN mass spectrum, m/e 604.9 (M−1 calculated for $C_{30}H_{30}N_4O_8S$: 605).

Example 17

Analogously to example 6, by saponification of {3-[4-(5-isopropenyl-pyridine-2-sulfonylamino)-6-methoxy-5-(2-methoxy-phenoxy)-pyrimidin-2-yl]-phenoxy}-acetic acid ethyl ester, product of example 16, with 1N aqueous NaOH in MeOH there was obtained {3-[4-(5-isopropenyl-pyridine-2-sulfonylamino)-6-methoxy-5-(2-methoxy-phenoxy)-pyrimidin-2-yl]-phenoxy}-acetic acid as an off-white solid. ISN mass spectrum, m/e 576.9 (M−1 calculated for $C_{28}H_{26}N_4O_8S$: 577).

Example 18

In analogy to example 7, by reduction of {3-[4-(5-isopropenyl-pyridine-2-sulfonylamino)-6-methoxy-5-(2-methoxy-phenoxy)-pyrimidin-2-yl]-phenoxy}-acetic acid ethyl ester, product of example 16, with $NaBH_4/CaCl_2$ there was obtained 5-isopropenyl-pyridine-2-sulfonic acid [2-[3-(2-hydroxy-ethoxy)-phenyl]-6-methoxy-5-(2-methoxy-phenoxy)-pyrimidin-4-yl]-amide as a white solid. ISN mass spectrum, m/e 563.2 (M−1 calculated for $C_{28}H_{28}N_4O_7S$: 563).

Example 19 a) To a suspension of 0.5 g of 5-methyl-pyridine-2-sulfonic acid [6-methoxy-5-(2-methoxy-phenoxy)-2-(1-oxy-pyridin-4-yl)-pyrimidin-4-yl]-amide in $CH_3CN$ (20 ml) were added at RT 1.26 ml of triethylamine followed by 0.9 ml of trimethylsilyl cyanide. The mixture was then refluxed for 20 h, cooled to RT and partitioned between water, acidic acid and EtOAc. The organic layer was washed twice with water, dried over $NaSO_4$ and the organic solvent was then removed in vacuo. The residue was purified on a silica gel chromatography column (eluted with $Me_2Cl_2$/MeOH: 95/5). Combination of the purified fractions and evacuation in vacuo afforded 5-methyl-pyridine-2-sulfonic acid [2-(2-cyano-pyridin-4-yl)-6-methoxy-5-(2-methoxy-phenoxy)-pyrimidin-4-yl]-amide as a off-white solid. ISP mass spectrum, m/e 505.2 (M+1 calculated for $C_{24}H_{20}N_5O_6S$: 505).

Preparation of the starting material:

b) A solution of 30 g of 4-[4,6-dichloro-5-(2-methoxy-phenoxy)-pyrimidin-2-yl]-pyridine 1-oxide and 31.1 g of 5-methyl-pyridyl-2-sulfonamide potassium salt (preparations described in EP 0 799 209) in DMSO (100 ml) was stirred for 20 h art RT. The reaction mixture was slowly poured into a mixture of water/$Et_2O$ (each 100 ml) under vigorous stirring, the precipitate was filtered off, suspended in EtOAc (1 l) and treated with 2N aq. HCl (37.5 ml) for 15 minutes under vigorous stirring. The crystalline solid was filtered off by suction and dried foe 12 h in a high vacuum to give 5-methyl-pyridine-2-sulfonic acid 6-chloro-5-(2-methoxy-phenoxy)-2-(1-oxy-pyridin-4-yl)-pyrimidin-4-ylamide as off-white crystals, mp 239°–240° C., crystallised from AcOEt.

c) To a solution of 1.83 g sodium in MeOH (50 ml) were added 4 g of 5-methyl-pyridine-2-sulfonic acid 6-chloro-5-(2-methoxy-phenoxy)-2-(1-oxy-pyridin-4-yl)-pyrimidin-4-ylamide at RT and the mixture was then refluxed for 20 h until completion of the reaction. The mixture was then poured on cold 1N aqueous HCL and the product extracted into $CH_2Cl_2$. The organic layer was dried over $Na_2SO_4$ and the solvent removed in vacuo. The crude product was crystallised from $Et_2O$/AcOEt (1:1) to give 5-methyl-pyridine-2-sulfonic acid [6-methoxy-5-(2-methoxy-phenoxy)-2-(1-oxy-pyridin-4-yl)-pyrimidin-4-yl]-amide as off-white crystals. ISP mass spectrum, m/e 496.1 (M+1 calculated for $C_{23}H_{21}N_5O_6S$: 496).

Example 20

0.356 g of 5-methyl-pyridine-2-sulfonic acid [2-(2-cyano-pyridin-4-yl)-6-methoxy-5-(2-methoxy-phenoxy)-pyrimidin-4-yl]-amide, product of example 19, dissolved in EtOH (5 ml) were treated at RT with 2N NaOH (0.7 ml) and the solution was refluxed for 30 minutes until the transformation was complete according to TLC analysis. The reaction mixture was cooled to 0° C., the pH adjusted to pH=1. The crystalline solid was filtered off, washed with water and dried in a high vacuum to provide the desired 4-[4-methoxy-5-(2-methoxy-phenoxy)-6-(5-methyl-pyridine-2-sulfonylamino)-pyrimidin-2-yl]-pyridine-2-carboxylic acid amide as an off-white solid. ISN mass spectrum, m/e 521.1 (M−1 calculated for $C_{24}H_{22}N_6O_6S$: 521).

Example 21

1 g of 4-[4-methoxy-5-(2-methoxy-phenoxy)-6-(5-methyl-pyridine-2-sulfonylamino)-pyrimidin-2-yl]-pyridine-2-carboxylic acid amide, product of example 20, dissolved in a mixture of THF/dioxane (40 ml/30 ml) were treated at RT with 3N HCl (40 ml) and the solution was refluxed for 24 h, further THF (12 ml) and 3M HCl (12 ml) was then added and the solution was heated to reflux for further 24 h until the transformation was complete according to TLC analysis. The reaction mixture was concentrated in vacuo and the product was extracted into $CH_2Cl_2$. The organic layer was dried over $Na_2SO_4$, the solvent removed in vacuo. The remaining crystalline solid was washed with ether and dried in a vacuum to give 4-[4-methoxy-5-(2-methoxy-phenoxy)-6-(5-methyl-pyridine-2-sulfonylamino)-pyrimidin-2-yl]-pyridine-2-carboxylic acid as an off-white solid. ISN mass spectrum, m/e 522 (M−1 calculated for $C_{24}H_{21}N_5O_7S$: 522).

Example 22

220 mg of 4-[4-methoxy-5-(2-methoxy-phenoxy)-6-(5-methyl-pyridine-2-sulfonylamino)-pyrimidin-2-yl]-pyridine-2-carboxylic acid, product of example 21, suspended in acetontrile (10 ml) was treated at RT subsequently with 27 mg of methanol, 100 mg of 4-(dimethylamino) pyridine (DMAP) and 186 mg of benzotriazol-1-yloxytris-(dimethylamino)-phosphonium hexafluorophosphate (BOP). The mixture was stirred for 12 h at RT, then partitioned between cold diluted HCl and EtOAc. The layers were separated, the organic layer dried over $Na_2SO_4$ and the solvent removed in vacuo. The residue was purified on a silica gel chromatography column (eluted with $Me_2Cl_2$/MeOHc: 95/5). Combination of the purified fractions and evacuation in vacuo afforded 4-[4-methoxy-5-(2-methoxy-phenoxy)-6-(5-methyl-pyridine-2-sulfonylamino)-pyrimidin-2-yl]-pyridine-2-carboxylic acid methyl ester as a white solid. ISN mass spectrum, m/e 536.2 (M−1 calculated for $C_{25}H_{23}N_5O_7S$: 536).

Example 23

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and ethanol there was obtained 4-[4-methoxy-5-(2-methoxy-phenoxy)-6-(5-methyl-pyridine-2-sulfonylamino)-pyrimidin-2-yl]-pyridine-2-carboxylic acid ethyl ester as a white solid. ISN mass spectrum, m/e 550.1 (M−1 calculated for $C_{26}H_{25}N_5O_7S$: 550).

Example 24

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and isopropanol there was obtained 4-[4-methoxy-5-(2-methoxy-phenoxy)-6-(5-methyl-pyridine-2-sulfonylamino)-pyrimidin-2-yl]-pyridine-2-carboxylic acid isopropyl ester as a white solid. ISN mass spectrum, m/564.2 (M−1 calculated for $C_{27}H_{27}N_5O_7S$: 564).

Example 25

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and ethylenglycol there was obtained 4-[4-methoxy-5-(2-methoxy-phenoxy)-6-(5-methyl-pyridine-2- sulfonylamino)-pyrimidin-2-yl]-pyridine-2-carboxylic acid 2-hydroxy-ethyl ester as a white solid. ISN mass spectrum, m/e 566.1 (M−1 calculated for $C_{26}H_{25}N_5O_8S$: 566).

Example 26

70 mg of 4-[4-methoxy-5-(2-methoxy-phenoxy)-6-(5-methyl-pyridine-2-sulfonylamino)-pyrimidin-2-yl]-pyridine-2-carboxylic acid, product of example 21, dissolved in DMF (5 ml) was treated at RT with 30 mg of 4-methylmorpholine, then cooled to 0° C. and further treated with 26 mg of 2-chloro-4,6-dimethoxy-1,3,5-triazine followed. The solution was stirred at RT for 90 minutes, then treated with 10 mg of metylamine hydrochloride and stirred for 12 h at RT. The mixture was partitioned between cold diluted HCl and EtOAc. The layers were separated, the organic layer washed with water, dried over $Na_2SO_4$ and the solvent was removed in vacuo. The solid residue was triturated with ether, filtered off and dried in a high vacuum to give 4-[4-methoxy-5-(2-methoxy-phenoxy)-6-(5-methyl-pyridine-2-sulfonylamino)-pyrimidin-2-yl]-pyridine-2-carboxylic acid methyl amide as a white crystalline solid. ISN mass spectrum, m/e 535.2 (M−1 calculated for $C_{25}H_{24}N_6O_6S$: 535).

Example 27

In analogy to example 26, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and ethanolamine, whereas the crude product was purified by column chromatography with $CH_2Cl_2$/MeOH (95/5) as eluent, there was obtained 4-[4-methoxy-5-(2-methoxy-phenoxy)-6-(5-methyl-pyridine-2-sulfonylamino)-pyrimidin-2-yl]-pyridine-2-carboxylic acid (2-hydroxy-ethyl)-amide as a white solid. ISN mass spectrum, m/e 566.1 (M−1 calculated for $C_{26}H_{26}N_6O_7S$: 566).

Example 28

In analogy to example 26, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and isopropylamine, whereas the crude product was purified by column chromatography with AcOEt as eluent, there was obtained 4-[4-methoxy-5-(2-methoxy-phenoxy)-6-(5-methyl-pyridine-2-sulfonylamino)-pyrimidin-2-yl]-pyridine-2-carboxylic acid isopropylamide as a white solid. ISN mass spectrum, m/e 563.2 (M−1 calculated for $CH_{27}H_{28}N_6O_6S$: 563).

Example 29

100 mg of 4-[4-methoxy-5-(2-methoxy-phenoxy)-6-(5-methyl-pyridine-2-sulfonylamino)-pyrimidin-2-yl]-pyridine-2-carboxylic acid methyl ester, product of example 22, were dissolved in a mixture of EtOH/THF (each 15 ml) on gentle warming and subsequently treated with 42 mg of $CaCl_2$ and 28 mg of $NaBH_4$ at RT. The reaction mixture was stirred at RT for 18 h until which time starting material was consumed according to TLC analysis. The mixture was partitioned between diluted HCl and $CH_2Cl_2$. The organic layer was dried over $Na_2SO_4$ and the solvent removed in vacuo to give 5-methyl-pyridine-2-sulfonic acid [2-(2-hydroxymethyl-pyridin-4-yl)-6-methoxy-5-(2-methoxy-phenoxy)-pyrimidin-4-yl]-amide as a white solid. ISN mass spectrum, m/e 508.3 (M−1 calculated for $C_{24}H_{23}N_5O_6S$: 508).

Example 30 a) To a solution of 6.6 mg of acetic acid and 22.3 mg of 4-methylmorpholin in DMF (5 ml) were added under ice-cooling 22.3 g of 2-Chloro-4,6-dimethoxy-1,3,5,-triazine and the solution was then stirred for 90 minutes at RT. Then 60 mg of 5-methyl-pyridine-2-sulfonic acid [2-(2-aminomethyl-pyridin-4-yl)-6-methoxy-5-(2-methoxy-phenoxy)-pyrimidin-4-yl]-amide hydrochloride were added and stirring was continued for 12 h at RT. The mixture was partitioned between cold diluted HCl and EtOAc. The layers were separated the organic layer washed with water, dried over $Na_2SO_4$ and the solvent removed in vacuo to give N-{4-[4-methoxy-5-(2-methoxy-phenoxy)-6-(5-methyl-pyridine-2-sulfonylamino)-pyrimidin-2-yl]-pyridin-2-ylmethyl}-acetamide as a light yellow crystalline solid. ISN mass spectrum, m/e 549.1 (M−1 calculated for $C_{26}H_{26}N_6O_6S$: 549).

Preparation of the starting material:

b) A solution of 100 mg of 5-methyl-pyridine-2-sulfonic acid [2-(2-cyano-pyridin-4-yl)-6-methoxy-5-(2-methoxy-phenoxy)-pyrimidin-4-yl]-amide, product of example 19, dissolved in MeOH (5 ml), was treated with 47.5 mg of benzyl chloride, 10 mg of palladium on charcoal (10%) and then hydrogenated at RT for hours until TLC analysis indicated completion of transformation. The catalyst was filtered off, and the solution concentrated in vacuo. The crystalline solid that precipitated was collected by filtration, washed with ether and dried in a high vacuum to give 5-methyl-pyridine-2-sulfonic acid [2-(2-aminomethyl-pyridin-4-yl)-6-methoxy-5-(2-methoxy-phenoxy)-pyrimidin-4-yl]-amide hydrochloride as light yellow crystals. ISP mass spectrum, m/e 509.3 (M+1 calculated for $C_{24}H_{24}N_6O_5S$: 509).

Example 31

A solution of 70 mg of 5-methyl-pyridine-2-sulfonic acid [2-(2-aminomethyl-pyridin-4-yl)-6-methoxy-5-(2-methoxy-phenoxy)-pyrimidin-4-yl]-amide hydrochloride, product of example 30 b), in $CH_2Cl_2$ (5 ml), was treated at RT with 50 mg of N-ethyldiisopropylamine, 15 mg of methanesulfonyl chloride and then refluxed for 18 h until the reaction was complete according to TLC analysis ($CH_2Cl_2$/MeOH: 95/5). The mixture was poured into cold diluted HCl and the product extracted into $CH_2Cl_2$. The organic layer was dried over $Na_2SO_4$ and the solvent removed in vacuo. The residue was purified on a silica gel chromatography column (eluted with $Me_2Cl_2$/MeOH: 95/5). Combination of the purified fractions and evacuation in vacuo afforded 5-methyl-pyridine-2-sulfonic acid [2-[2-(methanesulfonylamino-methyl)-pyridin-4-yl]-6-methoxy-5-(2-methoxy-phenoxy)-pyrimidin-4-yl]-amide as a light yellow solid. ISN mass spectrum, m/e 585 (M−1 calculated for $C_{25}H_{26}N_6O_7S_2$: 585).

Example 32

In analogy to example 31, 5-methyl-pyridine-2-sulfonic acid [2-(2-aminomethyl-pyridin-4-yl)-6-methoxy-5-(2-methoxy-phenoxy)-pyrimidin-4-yl]-amide hydrochloride, product of example 30 b), and ethanesulfonyl chloride, there was obtained 5-methyl-pyridine-2-sulfonic acid [2-[2-(ethanesulfonylamino-methyl)-pyridin-4-yl]-6-methoxy-5-(2-methoxy-phenoxy)-pyrimidin-4-yl]-amide as a light brown solid. ISN mass spectrum, m/e 599 (M−1 calculated for $C_{26}H_{28}N_6O_7S_2$: 599).

Example 33

A solution of 70 mg of 5-methyl-pyridine-2-sulfonic acid [2-(2-aminomethyl-pyridin-4-yl)-6-methoxy-5-(2-methoxyphenoxy)-pyrimidin-4-yl]-amide hydrochloride, product of example 30 b), in toluene (5 ml), was treated at RT with 26 mg of triethyamine then with 10 mg of ethylisocyanate and refluxed for 1 h until the reaction was complete according to TLC analysis ($CH_2Cl_2$/MeOH: 95/5). The mixture was poured into cold diluted HCl and the product extracted into $CH_2Cl_2$. The organic layer was dried over $Na_2SO_4$ and the solvent removed in vacuo. The solid residue was crystallised from $CH_2Cl_2$/$Et_2O$ to afford 5-methyl-pyridine-2-sulfonic acid [2-{2-[(3-ethyl-ureido)-methyl]-pyridin-4-yl}-6-methoxy-5-(2-methoxy-phenoxy)-pyrimidin-4-yl]-amide as off-white crystals. ISP mass spectrum, m/e 580.1 (M+1 calculated for $C_{27}H_{29}N_7O_6S$: 580).

Example 34

A suspension of 100 mg of 5-methyl-pyridine-2-sulfonic acid [2-(2-cyano-pyridin-4-yl)-6-methoxy-5-(2-methoxy-phenoxy)-pyrimidin-4-yl]-amide, product of example 19, in dioxane (10 ml) was treated at RT with 0.17 ml of N-etyldiisopropylamine then with 69 mg of hydroxylamine hydrochloride and refluxed 12 h until the reaction was complete according to TLC analysis. The mixture was poured into cold diluted HCl and the product extracted into AcOEt. The organic layer was dried over $Na_2SO_4$ and the solvent removed in vacuo. The solid residue was crystallised from $CH_2Cl_2$/Et2O to afford N-hydroxy-4-[4-methoxy-5-(2-methoxy-phenoxy)-6-(5-methyl-pyridine-2-sulfonylamino)-pyrimidin-2-yl]-pyridine-2-carboxamidine as off-white crystals. ISN mass spectrum, m/e 536.2 (M−1 calculated for $C_{24}H_{23}N_7O_6S$: 536).

Example 35

A solution of 108 mg of N-hydroxy-4-[4-methoxy-5-(2-methoxy-phenoxy)-6-(5-methyl-pyridine-2-sulfonylamino)-pyrimidin-2-yl]-pyridine-2-carboxamidine, product of example 34, in acetic acid (3 ml) was treated at RT with 0.057 ml of acetic anhydride then and refluxed for 12 h. The reaction mixture was partitioned between $CH_2Cl_2$ and diluted aqueous $KHCO_3$, the organic layer was dried over $Na_2SO_4$ and the solvent was removed in a vacuo. The residue was purified on a silica gel chromatography column (eluted with AcOEt). Combination of the purified fractions and evacuation in vacuo afforded 5-methyl-pyridine-2-sulfonic acid {6-methoxy-5-(2-methoxy-phenoxy)-2-[2-(5-methyl-[1,2,4]oxadiazol-3-yl)-pyridin-4-yl]-pyrimidin-4-yl}-amide as a light yellow solid. ISN mass spectrum, m/e 560.1 (M−1 calculated for $C_{26}H_{23}N_7O_6S$: 560).

Example 36

170 mg of 5-methyl-pyridine-2-sulfonic acid [6-methoxy-5-(2-methoxy-phenoxy)-2-(1-oxy-pyridin-4-yl)-pyrimidin-4-yl]-amide, product of example 19 c), in ethylenglycol (10 ml) were treated under ice-cooling with 0.14 ml of trietylamine and 85 mg of tosyl chloride. The ice-bath was removed and the reaction mixture was stirred at 50° C. for 18 h. The mixture was partitioned between 10% $NH_4Cl$ and EtOAc. The organic layer was separated, dried over $Na_2SO_4$ and the solvent was removed in vacuo. The residue was purified on a silica gel chromatography column (eluted with EtOAc). Combination of the purified fractions and evacuation in vacuo afforded 5-methyl-pyridine-2-sulfonic acid [2-[2-(2-hydroxy-ethoxy)-pyridin-4-yl]-6-methoxy-5-(2-methoxy-phenoxy)-pyrimidin-4-yl]-amide as a white solid. ISP mass spectrum, m/e 540.3 (M+1 calculated for $C_{25}H_{25}N_5O_7S$: 540).

Example 37

In analogy to example 36, from 5-methyl-pyridine-2-sulfonic acid [6-methoxy-5-(2-methoxy-phenoxy)-2-(1-oxy-pyridin-4-yl)-pyrimidin-4-yl]-amide, product of example 19c), and methanol there was obtained 5-methyl-pyridine-2-sulfonic acid [6-methoxy-5-(2-methoxy-phenoxy)-2-(2-methoxy-pyridin-4-yl)-pyrimidin-4-yl]-amide as a light yellow solid. ISP mass spectrum, m/e 510.3 (M+1 calculated for $C_{24}H_{23}N_5O_6S$: 510).

Example 38

In analogy to example 36, from 5-methyl-pyridine-2-sulfonic acid [6-methoxy-5-(2-methoxy-phenoxy)-2-(1-oxy-pyridin-4-yl)-pyrimidin-4-yl]-amide, product of example 19c), and ethanol there was obtained 5-methyl-pyridine-2-sulfonic acid [2-(2-ethoxy-pyridin-4-yl)-6-methoxy-5-(2-methoxy-phenoxy)-pyrimidin-4-yl]-amide as a off-white solid. ISP mass spectrum, m/e 524.2 (M+1 calculated for $C_{25}H_{25}N_5O_6S$: 524).

Example 39

In analogy to example 36, from 5-methyl-pyridine-2-sulfonic acid [6-methoxy-5-(2-methoxy-phenoxy)-2-(1-oxy-pyridin-4-yl)-pyrimidin-4-yl]-amide, product of example 19c), and allylalkohol there was obtained 5-methyl-pyridine-2-sulfonic acid [2-(2-allyloxy-pyridin-4-yl)-6-methoxy-5-(2-methoxy-phenoxy)-pyrimidin-4-yl]-amide as a light yellow solid. ISN mass spectrum, m/e 534.2 (M−1 calculated for $C_{26}H_{25}N_5O_6S$: 534).

Example 40

60 mg of 5-methyl-pyridine-2-sulfonic acid [2-(2-allyloxy-pyridin-4-yl)-6-methoxy-5-(2-methoxy-phenoxy)-pyrimidin-4-yl]-amide, product of example 39, were suspended in THF (5 ml), treated at RT with 2.2 mg of tetrakis-(triphenylphosphine)palladium and stirred for 5 minutes after which time 6.4 mg of $NaBH_4$ were added. The mixture was stirred for 2 h until the reaction was completed according to TLC analysis. The reaction mixture was poured into cold diluted HCl, the product extracted into AcOEt. The organic layer was dried over $NaSO_4$ and the solvent removed in vacuo to give 5-methyl-pyridine-2-sulfonic acid [2-(2-hydroxy-pyridin-4-yl)-6-methoxy-5-(2-methoxy-phenoxy)-pyrimidin-4-yl]-amide as a light yellow solid. ISN mass spectrum, m/e 494.1 (M−1 calculated for $C_{23}H_{21}N_5O_6S$: 494).

Example 41 a) To a solution of 2.93 g of 4-[4-(5-isopropyl-pyridine-2-sulfonylamino)-6-methoxy-5-(2-methoxy-phenoxy)-pyrimidin-2-yl]-pyridine-2-carboximidic acid methyl ester sodium salt in DMF (60 ml) was added under ice cooling NaH (0.8 g of a 60% NaH suspension in oil). The mixture was stirred for 1,5 h at 0° C. The mixture was poured into water, the pH adjusted to pH=6 and the product extracted into EtOAc. The organic layer was washed with water, dried over $Na_2SO_4$ and the solvent removed in vacuo. The residue was purified on a silica gel chromatography column (eluted with $Me_2Cl_2$/EtOAc: 5/1). Combination of the purified fractions and evacuation in vacuo afforded 5-isopropyl-pyridine-2-sulfonic acid [2-(2-cyano-pyridin-4-yl)-6-methoxy-5-(2-methoxy-phenoxy)-pyrimidin-4-yl]-amide as a light yellow crystalline solid. ISN mass spectrum, m/e 531.1 (M−1 calculated for $C_{26}H_{24}N_6O_5S$: 531).

Preparation of the starting material:

b) In analogy to example 1g), from 5-isopropylmethylpyridyl-2-sulfonamide potassium salt (preparation described in EP 713'875 and Bioorg. Med.

Chem. Lett., 1997, 7, 2223–2228) and 4-[4,6-dichloro-5-(2-methoxy-phenoxy)-pyrimidin-2-yl]-pyridine-2-carbonitrile there was obtained 5-isopropyl-pyridine-2-sulfonic acid [6-chloro-2-(2-cyano-pyridin-4-yl)-5-(2-methoxy-phenoxy)-pyrimidin-4-yl]-amide as a light brown solid of mp 255°–259° C.

The starting material 4-[4,6-dichloro-5-(2-methoxy-phenoxy)-pyrimidin-2-yl]-pyridine-2-carbonitrile was prepared from 5-(2-methoxy-phenoxy)-2-(pyridin-4-yl)-pyrimidine-4,6-diol (EP 0 799 209) by carbamoyl introduction with formamide in water and with $H_2O_2/FeSO_4$ as reagents in a Minisci-type radical reaction (Minisci et al, Tetrahedron, 41, 4157. 1985) to give 4-[4,6-dihydroxy-5-(2-methoxy-phenoxy)-pyrimidin-2-yl]-pyridine-2-carboxylic acid amide as a beige crystalline solid, crystallised from $DMF/H_2O$. Treatment with $POCl_3$ in analogy to example 1f) afforded 4-[4,6-dichloro-5-(2-methoxy-phenoxy)-pyrimidin-2-yl]-pyridine-2-carbonitrile as a beige solid, mp 211°–212° C., crystallised from $AcOEt/CH_2Cl_2$.

c) To a solution of 2.29 g of sodium in MeOH (250 ml) were added 5.37 g of 5-isopropyl-pyridine-2-sulfonic acid [6-chloro-2-(2-cyano-pyridin-4-yl)-5-(2-methoxy-phenoxy)-pyrimidin-4-yl]-amide at RT and the mixture was then refluxed for 20 h until completion of the reaction. The mixture was then poured into water and the product extracted into $CH_2Cl_2$. The organic layer was dried over $Na_2SO_4$ and the solvent removed in vacuo. The solid residue was triturated with ether filtered off under suction and dried in a high vacuum to give 4-[4-(5-isopropyl-pyridine-2-sulfonylamino)-6-methoxy-5-(2-methoxy-phenoxy)-pyrimidin-2-yl]-pyridine-2-carboximidic acid methyl ester sodium salt as light brown solid. ISN mass spectrum, m/e 563.2 (M−1 calculated for $C_{27}H_{27}N_6O_6S$: 563 for free sulfonamide).

Example 42

In analogy to example 20, from 5-isopropyl-pyridine-2-sulfonic acid [2-(2-cyano-pyridin-4-yl)-6-methoxy-5-(2-methoxy-phenoxy)-pyrimidin-4-yl]-amide, product of example 41, by treatment with 2N NaOH there was obtained 4-[4-(5-isopropyl-pyridine-2-sulfonylamino)-6-methoxy-5-(2-methoxy-phenoxy)-pyrimidin-2-yl]-pyridine-2-carboxylic acid amide as an off-white solid. ISN mass spectrum, m/e 549.1 (M−1 calculated for $C_{26}H_{26}N_6O_6S$: 549).

Example 43

To 0.586 g of 4-[4-(5-isopropyl-pyridine-2-sulfonylamino)-6-methoxy-5-(2-methoxy-phenoxy)-pyrimidin-2-yl]-pyridine-2-carboximidic acid methyl ester sodium salt, product of example 41 c), in methanol (10 ml) were added 6 N HCl (3 ml) and the mixture was refluxed for 1 h until the reaction was complete according to TLC analysis (eluent: $CH_2CL_2/EtOAc$: 4/1). The mixture was poured into water and the product extracted into EtOAc. The organic layer was washed with water, dried over $Na_2SO_4$ and the solvent removed in vacuo. The residue was purified on a silica gel chromatography column (eluted with $Me_2Cl_2/EtOAc$: 4/1). Combination of the purified fractions and evacuation in vacuo afforded 4-[4-(5-isopropyl-pyridine-2-sulfonylamino)-6-methoxy-5-(2-methoxy-phenoxy)-pyrimidin-2-yl]-pyridine-2-carboxylic acid methyl ester as an off-white solid. ISN mass spectrum, m/e 564.2 (M−1 calculated for $C_{27}H_{27}N_5O_7S$: 564).

Example 44

In analogy to example 29, by reduction of 4-[4-(5-isopropyl-pyridine-2-sulfonylamino)-6-methoxy-5-(2-methoxy-phenoxy)-pyrimidin-2-yl]-pyridine-2-carboxylic acid methyl ester, product of example 43, with $NaBH_4$ in the presence of $CaCl_2$ there was obtained 5-isopropyl-pyridine-2-sulfonic acid [2-(2-hydroxymethyl-pyridin-4-yl)-6-methoxy-5-(2-methoxy-phenoxy)-pyrimidin-4-yl]-amide as a white solid. ISN mass spectrum, m/e 536.2 (M−1 calculated for $C_{26}H_{27}N_5O_6S$: 536).

Example 45

To a solution of 56.6 mg of 4-[4-(5-isopropyl-pyridine-2-sulfonylamino)-6-methoxy-5-(2-methoxy-phenoxy)-pyrimidin-2-yl]-pyridine-2-carboxylic acid methyl ester, product of example 43, there were added at RT 0.5 ml of 1N NaOH and the solution was stirred for 1 h until the reaction was complete according to TLC analysis. It was then poured into cold diluted HCl and the product was extracted into EtOAc. The organic layer was washed with water, dried over $Na_2SO_4$ and the solvent removed in vacuo. The solid residue was washed with ether then dried in a high vacuum to give 4-[4-(5-isopropyl-pyridine-2-sulfonylamino)-6-methoxy-5-(2-methoxy-phenoxy)-pyrimidin-2-yl]-pyridine-2-carboxylic acid as a light yellow crystalline solid. ISN mass spectrum, m/e 550.1 (M−1 calculated for $C_{26}H_{25}N_5O_7S$: 550).

Example 46

In analogy to example 22, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and ethanol there was obtained 4-[4-(5-isopropyl-pyridine-2-sulfonylamino)-6-methoxy-5-(2-methoxy-phenoxy)-pyrimidin-2-yl]-pyridine-2-carboxylic acid ethyl ester as a white solid. ISN mass spectrum, m/e 578 (M−1 calculated for $C_{28}H_{29}N_5O_7S$: 578).

Example 47

In analogy to example 22, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and isopropanol there was obtained 4-[4-(5-isopropyl-pyridine-2-sulfonylamino)-6-methoxy-5-(2-methoxy-phenoxy)-pyrimidin-2-yl]-pyridine-2-carboxylic acid isopropyl ester as a white solid. ISN mass spectrum, m/e 592.1 (M−1 calculated for $C_{29}H_{31}N_5O_7S$: 592).

Example 48

In analogy to example 26, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and methylamine hydrochloride there was obtained 4-[4-(5-isopropyl-pyridine-2-sulfonylamino)-6-methoxy-5-(2-methoxy-phenoxy)-pyrimidin-2-yl]-pyridine-2-carboxylic acid methylamide as a white solid. ISN mass spectrum, m/e 563.2 (M−1 calculated for $C_{27}H_{28}N_6O_6S$: 563).

Example 49

In analogy to example 26, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and ethanolamine there was obtained 4-[4-(5-isopropyl-pyridine-2-sulfonylamino)-6-methoxy-5-(2-methoxy-phenoxy)-pyrimidin-2-yl]-pyridine-2-carboxylic acid (2-hydroxy-ethyl)-amide as a white solid.

ISN mass spectrum, m/e 593.1 (M−1 calculated for $C_{28}H_{30}N_6O_6S$ 593).

Example 50

In analogy to example 26, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and isopropylamine there was obtained 4-[4-(5-isopropyl-pyridine-2-sulfonylamino)-6-methoxy-5-(2-methoxy-phenoxy)-pyrimidin-2-yl]-pyridine-2-carboxylic acid isopropylamide as a white solid. ISP mass spectrum, m/e 593.2 (M+1 calculated for $C_{29}H_{32}N_6O_6S$: 593).

Example 51

In analogy to example 26, from 4-[4-(5-isopropyl-pyridine-2-sulfonylamino)-6-methoxy-5-(2-methoxy-phenoxy)-pyrimidin-2-yl]-pyridine-2-carboxylic acid, product of example 45, and dimetylamine hydrochloride there was obtained 4-[4-(5-isopropyl-pyridine-2-sulfonylamino)-6-methoxy-5-(2-methoxy-phenoxy)-pyrimidin-2-yl]-pyridine-2-carboxylic acid dimethylamide as a white solid. ISP mass spectrum, m/e 579.1 (M+1 calculated for $C_{28}H_{30}N_6O_6S$: 579).

Example 52 a) In analogy to example 30a), from 5-isopropyl-pyridine-2-sulfonic acid [2-(2-aminomethyl-pyridin-4-yl)-6-methoxy-5-(2-methoxy-phenoxy)-pyrimidin-4-yl]-amide hydrochloride and acetic acid there was obtained N-{4-[4-(5-isopropyl-pyridine-2-sulfonylamino)-6-methoxy-5-(2-methoxy-phenoxy)-pyrimidin-2-yl]-pyridin-2-ylmethyl}-acetamide as an off-white crystalline solid. ISP mass spectrum, m/e 579.1 (M+1 calculated for $C_{28}H_{30}N_6O_6S$: 579).

Preparation of staring material:

b) In analogy to example 30 b), by hydrogenation of 5-isopropyl-pyridine-2-sulfonic acid [2-(2-cyano-pyridin-4-yl)-6-methoxy-5-(2-methoxy-phenoxy)-pyrimidin-4-yl]-amide, product of example 41, there was obtained 5-isopropyl-pyridine-2-sulfonic acid [2-(2-aminomethyl-pyridin-4-yl)-6-methoxy-5-(2-methoxy-phenoxy)-pyrimidin-4-yl]-amide hydrochloride as a light yellow solid. ISN mass spectrum, m/e 535.2 (M−1 calculated for $C_{26}H_{28}N_6O_5S$: 535, free amine).

Example 53

In analogy to example 31, from 5-isopropyl-pyridine-2-sulfonic acid [2-(2-aminomethyl-pyridin-4-yl)-6-methoxy-5-(2-methoxy-phenoxy)-pyrimidin-4-yl]-amide hydrochloride, product of example 52 b), and methanesulfonyl chloride acid there was obtained 5-isopropyl-pyridine-2-sulfonic acid [2-[2-(methanesulfonylamino-methyl)-pyridin-4-yl]-6-methoxy-5-(2-methoxy-phenoxy)-pyrimidin-4-yl]-amide as an off-white solid. ISN mass spectrum, m/e 613.1 (M−1 calculated for $C_{27}H_{30}N_6O_7S_2$: 613).

Example 54

In analogy to example 33, from 5-isopropyl-pyridine-2-sulfonic acid [2-(2-aminomethyl-pyridin-4-yl)-6-methoxy-5-(2-methoxy-phenoxy)-pyrimidin-4-yl]-amide hydrochloride, product of example 52 b), and ethylisocyanate there was obtained 5-isopropyl-pyridine-2-sulfonic acid [2-{2-[(3-ethyl-ureido)-methyl]-pyridin-4-yl}-6-methoxy-5-(2-methoxy-phenoxy)-pyrimidin-4-yl]-amide as a yellow solid. ISN mass spectrum, m/e 606 (M−1 calculated for $C_{29}H_{33}N_7O_6S$: 606).

Example 55

In analogy to example 34, from 4-[4-(5-isopropyl-pyridine-2-sulfonylamino)-6-methoxy-5-(2-methoxy-phenoxy)-pyrimidin-2-yl]-pyridine-2-carboximidic acid methyl ester sodium salt, product of example 41 c), and hydroxylamine hydrochloride there was obtained N-hydroxy-4-[4-(5-isopropyl-pyridine-2-sulfonylamino)-6-methoxy-5-(2-methoxy-phenoxy)-pyrimidin-2-yl]-pyridine-2-carboxamidine as a light yellow crystalline salt. ISN mass spectrum, m/e 564.2 (M−1 calculated for $C_{26}H_{27}N_7O_6S$: 564).

Example 56

In analogy to example 35, from N-hydroxy-4-[4-(5-isopropyl-pyridine-2-sulfonylamino)-6-methoxy-5-(2-methoxy-phenoxy)-pyrimidin-2-yl]-pyridine-2-carboxamidine, product of example 55, and acetic anhydride in acetic acid there was obtained 5-isopropyl-pyridine-2-sulfonic acid {6-methoxy-5-(2-methoxy-phenoxy)-2-[2-(5-methyl-[1,2,4]oxadiazol-3-yl)-pyridin-4-yl]-pyrimidin-4-yl}-amide as a light yellow solid. ISN mass spectrum, m/e 588.2 (M−1 calculated for $C_{28}H_{27}N_7O_6S$: 588).

Example 57 a) In analogy to example 36, from 5-isopropyl-pyridine-2-sulfonic acid [6-methoxy-5-(2-methoxy-phenoxy)-2-(1-oxy-pyridin-4-yl)-pyrimidin-4-yl]-amide and ethylenglycol there was obtained 5-isopropyl-pyridine-2-sulfonic acid [2-[2-(2-hydroxy-ethoxy)-pyridin-4-yl]-6-methoxy-5-(2-methoxy-phenoxy)-pyrimidin-4-yl]-amide as a white solid. ISN mass spectrum, m/e 566.2 (M−1 calculated for $C_{27}H_{29}N_5O_7S$: 566).

Preparation of the starting material:

b) In analogy to example 19 b), from 5-isopropyl-pyridylsulfonamide potassium salt (preparation described in EP 0 799 209) and 4-[4,6-dichloro-5-(2-methoxy-phenoxy)-pyrimidin-2-yl]-pyridine 1-oxide there was obtained 5-isopropyl-pyridine-2-sulfonic acid 6-chloro-5-(2-methoxy-phenoxy)-2-(1-oxy-pyridin-4-yl)-pyrimidin-4-ylamide as a white solid crystallised from AcOEt. Melting point: 233–235° C.

c) In analogy to example 19 c), from 5-isopropyl-pyridine-2-sulfonic acid 6-chloro-5-(2-methoxy-phenoxy)-2-(1-oxy-pyridin-4-yl)-pyrimidin-4-ylamide and sodium methoxide there was obtained 5-isopropyl-pyridine-2-sulfonic acid [6-methoxy-5-(2-methoxy-phenoxy)-2-(1-oxy-pyridin-4-yl)-pyrimidin-4-yl]-amide as an off-white solid. ISP mass spectrum, m/e 524.1 (M+1 calculated for $C_{25}H_{25}N_5O_6S$: 524).

Example 58

In analogy to example 36, from 5-isopropyl-pyridine-2-sulfonic acid [6-methoxy-5-(2-methoxy-phenoxy)-2-(1-oxy-pyridin-4-yl)-pyrimidin-4-yl]-amide, product of example 57 c), and methanol there was obtained 5-isopropyl-pyridine-2-sulfonic acid [6-methoxy-5-(2-methoxy-phenoxy)-2-(2-methoxy-pyridin-4-yl)-pyrimidin-4-yl]-amide as a light yellow solid. ISN mass spectrum, m/e 536.2 (M−1 calculated for $C_{26}H_{27}N_5O_6S$: 536).

Example 59 a) In analogy to example 19, from 5-methyl-thiazole-2-sulfonic acid [6-methoxy-5-(2-methoxy-phenoxy)-2-(1- oxy-pyridin-4-yl)-pyrimidin-4-yl]-amide and trimethylsilyl cyanide there was obtained 5-methyl-thiazole-2-sulfonic acid [2-(2-cyano-pyridin-4-yl)-6-methoxy-5-(2-methoxy-phenoxy)-pyrimidin-4-yl]-amide as a light orange solid. ISN mass spectrum, m/e xxx,X (M−1 calculated for $C_{22}H_{18}N_6O_5S_2$: 509).

Preparation of the starting material:

b) In analogy to example 19 b, from 5-methyl-thiazole-2-sulfonic acid amide potassium salt, product of example 9 b), and 4-[4,6-dichloro-5-(2-methoxy-phenoxy)-pyrimidin-2-yl]-pyridine 1-oxide there was obtained 5-methyl-thiazole-2-sulfonic acid [6-chloro-5-(2-methoxy-phenoxy)-2-(1-oxy-pyridin-4-yl)-pyrimidin-4-yl]-amide as a light yellow solid. ISN mass spectrum, m/e 504 (M−1 calculated for $C_{20}H_{16}ClN_5O_5S_2$: 504).

c) In analogy to example 29 c, from 5-methyl-thiazole-2-sulfonic acid [6-chloro-5-(2-methoxy-phenoxy)-2-(1-oxy-pyridin-4-yl)-pyrimidin-4-yl]-amide and sodium methoxide there was obtained 5-methyl-thiazole-2-sulfonic acid [6-methoxy-5-(2-methoxy-phenoxy)-2-(1-oxy-pyridin-4-yl)-pyrimidin-4-yl]-amide as a light yellow solid. ISN mass spectrum, m/e 500.1 (M−1 calculated for $C_{21}H_{19}ClN_5O_6S_2$: 500).

Example 60

In analogy to example 20, from 5-methyl-thiazole-2-sulfonic acid [2-(2-cyano-pyridin-4-yl)-6-methoxy-5-(2-methoxy-phenoxy)-pyrimidin-4-yl]-amide, product of example 59, by treatment with 2N NaOH there was obtained 4-[4-methoxy-5-(2-methoxy-phenoxy)-6-(5-methyl-thiazole-2-sulfonylamino)-pyrimidin-2-yl]-pyridine-2-carboxylic acid amide as light yellow solid. ISN mass spectrum, m/e 527 (M+1 calculated for $C_{22}H_{20}N_6O_6S_2$: 527).

Example 61

In analogy to example 21, from 4-[4-methoxy-5-(2-methoxy-phenoxy)-6-(5-methyl-thiazole-2-sulfonylamino)-pyrimidin-2-yl]-pyridine-2-carboxylic acid amide, product of example 60, by treatment with 3N HCl in THF there was obtained 4-[4-methoxy-5-(2-methoxy-phenoxy)-6-(5-methyl-thiazole-2-sulfonylamino)-pyrimidin-2-yl]-pyridine-2-carboxylic acid as light yellow solid. ISN mass spectrum, m/e 528.2 (M−1 calculated for $C_{22}H_{19}N_5O_7S_2$: 528).

Example 62

In analogy to example 22, from 4-[4-methoxy-5-(2-methoxy-phenoxy)-6-(5-methyl-thiazole-2-sulfonylamino)-pyrimidin-2-yl]-pyridine-2-carboxylic acid, product of example 61, by coupling with MeOH and benzotriazol-1-yloxytris-(dimethylamino)-phosphonium hexafluorophosphate (BOP) as regent there was obtained 4-[4-methoxy-5-(2-methoxy-phenoxy)-6-(5-methyl-thiazole-2-sulfonylamino)-pyrimidin-2-yl]-pyridine-2-carboxylic acid methyl ester as an off-white solid. ISP mass spectrum, m/e 544.2 (M+1 calculated for $C_{23}H_{21}N_5O_7S_2$: 544).

Example 63

In analogy to example 36, from 5-methyl-thiazole-2-sulfonic acid [6-methoxy-5-(2-methoxy-phenoxy)-2-(1-oxy-pyridin-4-yl)-pyrimidin-4-yl]-amide, product of example 59 c), and ethylenglycol there was obtained 5-methyl-thiazole-2-sulfonic acid [2-[2-(2-hydroxy-ethoxy)-pyridin-4-yl]-6-methoxy-5-(2-methoxy-phenoxy)-pyrimidin-4-yl]-amide as an off-white solid. ISN mass spectrum, m/e 544.1 (M−1 calculated for $C_{23}H_{23}N_5O_7S_2$: 544).

Example 64

In analogy to example 36, from 5-methyl-thiazole-2-sulfonic acid [6-methoxy-5-(2-methoxy-phenoxy)-2-(1-oxy-pyridin-4-yl)-pyrimidin-4-yl]-amide, product of example 59 c), and MeOH there was obtained 5-methyl-thiazole-2-sulfonic acid [6-methoxy-5-(2-methoxy-phenoxy)-2-(2-methoxy-pyridin-4-yl)-pyrimidin-4-yl]-amide as an off-white solid. ISN mass spectrum, m/e 514.1 (M−1 calculated for $C_{22}H_{21}N_5O_6S_2$: 514).

Example 65 a) In analogy to example 19a), from ethane, 5-isopropenyl-pyridine-2-sulfonic acid [6-methoxy-5-(2-methoxy-phenoxy)-2-(1-oxy-pyridin-4-yl)-pyrimidin-4-yl]-amide and trimethylsilyl cyanide there was obtained 5-isopropenyl-pyridine-2-sulfonic acid [2-(2-cyano-pyridin-4-yl)-6-methoxy-5-(2-methoxy-phenoxy)-pyrimidin-4-yl]-amide as a light brown solid. ISN mass spectrum, m/e 529.2 (M−1 calculated for $C_{26}H_{22}N_6O_5S$: 529).

Preparation of the starting material:

b) In analogy to example 19 b), from 5-isopropenyl-pyridine-2-sulfonic acid amide potassium salt, product of example 15 b), and 4-[4,6-dichloro-5-(2-methoxy-phenoxy)-pyrimidin-2-yl]-pyridine 1-oxide there was obtained 5-isopropenyl-pyridine-2-sulfonic acid [6-chloro-5-(2-methoxy-phenoxy)-2-(1-oxy-pyridin-4-yl)-pyrimidin-4-yl]-amide as a light yellow solid. ISN mass spectrum, m/e 524.3 (M−1 calculated for $C_{24}H_{20}ClN_5O_5S$: 524).

c) In analogy to example 23 c, from 5-isopropenyl-pyridine-2-sulfonic acid [6-chloro-5-(2-methoxy-phenoxy)-2-(1-oxy-pyridin-4-yl)-pyrimidin-4-yl]-amide and sodium methoxide there was obtained 5-isopropenyl-pyridine-2-sulfonic acid [6-methoxy-5-(2-methoxy-phenoxy)-2-(1-oxy-pyridin-4-yl)-pyrimidin-4-yl]-amide as a light yellow solid. ISN mass spectrum, m/e 520.2 (M−1 calculated for $C_{25}H_{23}N_5O_6S$: 520).

Example 66 a) In analogy to example 43, by treatment of 4-[4-(5-isopropenyl-pyridine-2-sulfonylamino)-6-methoxy-5-(2-methoxy-phenoxy)-pyrimidin-2-yl]-pyridine-2-carboximidic acid methyl ester sodium salt with 2N HCl in MeOH there was obtained 4-[4-(5-isopropenyl-pyridine-2-sulfonylamino)-6-methoxy-5-(2-methoxy-phenoxy)-pyrimidin-2-yl]-pyridine-2-carboxylic acid methyl ester as a white solid. ISN mass spectrum, m/e 562.2 (M−1 calculated for $C_{27}H_{25}N_5O_7S$: 562.

Preparation of the starting material:

b) To 0.72 g of 5-isopropenyl-pyridine-2-sulfonic acid [2-(2-cyano-pyridin-4-yl)-6-methoxy-5-(2-methoxy-phenoxy)-pyrimidin-4-yl]-amide, product of example 65, in dry MeOH (20 ml) were added at RT 3.4 ml of a 1M NaOMe in dry MeOH and the solution was stirred at 50° C. for 5 h. Further 1.7 ml of above NaOMe solution were added and heating (50° C.) for 2 h was continued until completion of the reaction according to HPLC analysis. The solution was cooled to RT and concentrated in vacuo. The crystalline solid which precipitated was filtered off under suction and washed with ether to give 4-[4-(5-isopropenyl-pyridine-2-sulfonylamino)-6-methoxy-5-(2-methoxy-phenoxy)-pyrimidin-2-yl]-pyridine-2-carboximidic acid methyl ester sodium salt white crystals. ISN mass spectrum, m/e 561.3 (M−1 calculated for $C_{27}H_{26}N_6O_7S$: 561—for free sulfonamide.

Example 67

0.1 g of 4-[4-(5-isopropenyl-pyridine-2-sulfonylamino)-6-methoxy-5-(2-methoxy-phenoxy)-pyrimidin-2-yl]-pyridine-2-carboximidic acid methyl ester sodium salt, product of example 66 b), in MeOH (10 ml) were treated at RT with 1.8 ml 1N NaOH and the solution was stirred for 26 h at RT. After this time further 1.8 ml 1N NaOH were added and stirring was continued for further 20 h until the reaction was complete according to HPLC analysis. The solution was concentrated then poured into diluted aqueous HCl, the product was extracted into AcOEt. The organic layer was washed with water, dried over $Na_2SO_4$ and concentrated in vacuo. The crystalline precipitate that had formed was collected under suction and washed with ether to give 4-[4-(5-isopropenyl-pyridine-2-sulfonylamino)-6-methoxy-5-(2-methoxy-phenoxy)-pyrimidin-2-yl]-pyridine-2-carboxylic acid as light yellow crystals. ISN mass spectrum, m/e 548 (M−1 calculated for $C_{26}H_{23}N_5O_7S$: 548).

Example 68

In analogy to example 29, by reduction of 4-[4-(5-isopropenyl-pyridine-2-sulfonylamino)-6-methoxy-5-(2-methoxy-phenoxy)-pyrimidin-2-yl]-pyridine-2-carboxylic acid methyl ester, product of example 66, with $NaBH_4$ in the presence of $CaCl_2$ there was obtained 5-isopropenyl-pyridine-2-sulfonic acid [2-(2-hydroxymethyl-pyridin-4-yl)-6-methoxy-5-(2-methoxy-phenoxy)-pyrimidin-4-yl]-amide as a light yellow solid. ISN mass spectrum, m/e 534.2 (M−1 calculated for $C_{26}H_{25}N_5O_6S$: 534.

Example 69

In analogy to example 34, from 5-isopropenyl-pyridine-2-sulfonic acid [2-(2-cyano-pyridin-4-yl)-6-methoxy-5-(2-methoxy-phenoxy)-pyrimidin-4-yl]-amide, product of example 65, and hydroxylamine hydochloride there was obtained N-hydroxy-4-[4-(5-isopropenyl-pyridine-2-sulfonylamino)-6-methoxy-5-(2-methoxy-phenoxy)-pyrimidin-2-yl]-pyridine-2-carboxamidine as a light yellow solid. ISN mass spectrum, m/e 566.2 (M−1 calculated for $C_{26}H_{25}N_7O_6S$: 562).

Example 70

In analogy to example 35, from N-hydroxy-4-[4-(5-isopropenyl-pyridine-2-sulfonylamino)-6-methoxy-5-(2-methoxy-phenoxy)-pyrimidin-2-yl]-pyridine-2-carboxamidine, product of example 69, on treatment and acetic anhydride in acetic acid there was obtained 5-isopropenyl-pyridine-2-sulfonic acid {6-methoxy-5-(2-methoxy-phenoxy)-2-[2-(5-methyl-[1,2,4]oxadiazol-3-yl)-pyridin-4-yl]-pyrimidin-4-yl}-amide as a light brown solid. ISN mass spectrum, m/e 586.1 (M−1 calculated for $C_{28}H_{25}N_7O_6S$: 586).

Example 71

In analogy to example 20, from 5-isopropenyl-pyridine-2-sulfonic acid [2-(2-cyano-pyridin-4-yl)-6-methoxy-5-(2-methoxy-phenoxy)-pyrimidin-4-yl]-amide, product of example 65, on treatment with NaOH there was obtained 4-[4-(5-isopropenyl-pyridine-2-sulfonylamino)-6-methoxy-5-(2-methoxy-phenoxy)-pyrimidin-2-yl]-pyridine-2-carboxylic acid amide as a light brown solid. ISN mass spectrum, m/e 547.1 (M−1 calculated for $C_{26}H_{24}N_6O_6S$: 547)

Example 72

In analogy to example 26, from 4-[4-(5-isopropenyl-pyridine-2-sulfonylamino)-6-methoxy-5-(2-methoxy-phenoxy)-pyrimidin-2-yl]-pyridine-2-carboxylic acid, product of example 67, and methylamine hydrochloride there was obtained 4-[4-(5-isopropenyl-pyridine-2-sulfonylamino)-6-methoxy-5-(2-methoxy-phenoxy)-pyrimidin-2-yl]-pyridine-2-carboxylic acid methylamide as a white solid. ISN mass spectrum, m/e 561.2 (M−1 calculated for $C_{27}H_{26}N_6O_6S$: 561).

Example 73

In analogy to example 36, from 5-isopropenyl-pyridine-2-sulfonic acid [6-methoxy-5-(2-methoxy-phenoxy)-2-(1-oxy-pyridin-4-yl)-pyrimidin-4-yl]-amide, product of example 65 c), and ethylenglycol there was obtained 5-isopropenyl-pyridine-2-sulfonic acid [2-[2-(2-hydroxy-ethoxy)-pyridin-4-yl]-6-methoxy-5-(2-methoxy-phenoxy)-pyrimidin-4-yl]-amide as a light yellow solid. ISN mass spectrum, m/e 564.2 (M−1 calculated for $C_{27}H_{27}N_5O_7S$: 564).

Example 74 a) In analogy to example 66 a), by treatment of 4-[4-(5-isopropenyl-pyridine-2-sulfonylamino)-6-methoxy-5-(2-methoxy-phenoxy)-pyrimidin-2-yl]-pyridine-2-carboximidic acid ethyl ester sodium salt with 2N HCl in ethanol there was obtained 4-[4-(5-isopropenyl-pyridine-2-sulfonylamino)-6-methoxy-5-(2-methoxy-phenoxy)-pyrimidin-2-yl]-pyridine-2-carboxylic acid ethyl ester as a whit solid. ISN mass spectrum, m/e 575.9 (M−1 calculated for $C_{28}H_{27}N_5O_7S$: 576).

Preparation of the starting material:

b) In analogy to example 66 b), from 5-isopropenyl-pyridine-2-sulfonic acid [2-(2-cyano-pyridin-4-yl)-6-methoxy-5-(2-methoxy-phenoxy)-pyrimidin-4-yl]-amide, product of example 65, and NaOEt in dry ethanol there was obtained 4-[4-(5-isopropenyl-pyridine-2-sulfonylamino)-6-methoxy-5-(2-methoxy-phenoxy)-pyrimidin-2-yl]-pyridine-2-carboximidic acid ethyl ester sodium salt as a light brown solid. ISN mass spectrum, m/e 575.1 (M−1 calculated for $C_{28}H_{28}N_6O_6S$: 575—free sulfonamide).

Example 75 a) In analogy to example 19, from 5-(1-hydroxy-1-methyl-ethyl)-pyridine-2-sulfonic acid [6-methoxy-5-(2-methoxy-phenoxy)-2-(1-oxy-pyridin-4-yl)-pyrimidin-4-yl]-amide and trimethylsilyl cyanide there was obtained 5-(1-hydroxy-1-methyl-ethyl)-pyridine-2-sulfonic acid [2-(2-cyano-pyridin-4-yl)-6-methoxy-5-(2-methoxy-phenoxy)-pyrimidin-4-yl]-amide as a light brown solid. ISN mass spectrum, m/e 547.1 (M−1 calculated for $C_{26}H_{24}N_6O_5S$: 547).

Preparation of the starting material:

b) In analogy to example 19 b), from 5-(1-hydroxy-1-methyl-ethyl)-pyridine-2-sulfonic acid amide potassium salt, product of example 14 b), and 4-[4,6-Dichloro-5-(2-methoxy-phenoxy)-pyrimidin-2-yl]-pyridine 1-oxide there was obtained 5-(1-hydroxy-1-methyl-ethyl)-pyridine-2-sulfonic acid [6-chloro-5-(2-methoxy-phenoxy)-2-(1-oxy-pyridin-4-yl)-pyrimidin-4-yl]-amide as a white solid. ISP mass spectrum, m/e 544.1 (M+1 calculated for $C_{24}H_{22}ClN_5O_6S$: 544).

c) In analogy to example 19 b), from 5-(1-hydroxy-1-methyl-ethyl)-pyridine-2-sulfonic acid [6-chloro-5-(2- methoxy-phenoxy)-2-(1-oxy-pyridin-4-yl)-pyrimidin-4-yl]-amide and sodium methoxide there was obtained 5-(1-hydroxy-1-methyl-ethyl)-pyridine-2-sulfonic acid [6-methoxy-5-(2-methoxy-phenoxy)-2-(1-oxy-pyridin-4-yl)-pyrimidin-4-yl]-amide as a white solid. ISN mass spectrum, m/e 538.2 (M−1 calculated for $C_{25}H_{25}N_5O_7S$: 538).

Example 76

In analogy to example 36, from 5-(1-hydroxy-1-methyl-ethyl)-pyridine-2-sulfonic acid [6-methoxy-5-(2-methoxy-phenoxy)-2-(1-oxy-pyridin-4-yl)-pyrimidin-4-yl]-amide, product of example 75 c), and ethylenglycol there was obtained 5-(1-hydroxy-1-methyl-ethyl)-pyridine-2-sulfonic acid [2-[2-(2-hydroxy-ethoxy)-pyridin-4-yl]-6-methoxy-5-(2-methoxy-phenoxy)-pyrimidin-4-yl]-amide as a light yellow solid. ISN mass spectrum, m/e 582.4 (M−1 calculated for $C_{27}H_{29}N_5O_8S$: 582).

Example 77

To a solution of 0.52 g of 4-[4-methoxy-5-(2-methoxy-phenoxy)-6-(5-methyl-pyridine-2-sulfonylamino)-pyrimidin-2-yl]-pyridine-2-carboxylic acid, product of example 21, in DMF (10 ml) were added at RT 0.23 g of 1,1,3,3-tetramethylguanidine followed by 0,245 g of acetic acid 1-chloroethyl ester (preparation described by M. Ertan et al., Arzneim. Forsch. 1992, Vol. 42, 70). The reaction mixture was then heated at 60° C. for 20 h, cooled to RT and partitioned between ice water and EtOAc. The organic layer was washed with water, dried over $Na_2SO4$ and the organic layer was removed in vacuo. The residue was purified on a silica gel chromatography column (eluted with tert-butyl methyl ether). Combinations of the purified fractions and evacuation in vacuo afforded 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester as a white solid. ISN mass spectrum, m/e 608 (M−1 calculated for $C_{28}H_{27}N_5O_9S$: 608).

Example 78

In analogy to example 77, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and chloromethyl pivalate there was obtained 4-[4-methoxy-5-(2-methoxy-phenoxy)-6-(5-methyl-pyridine-2-sulfonylamino)-pyrimidin-2-yl]-pyridine-2-carboxylic acid 2,2-dimethyl-propionyloxymethyl ester as a white solid. ISN mass spectrum, m/e 636 (M−1 calculated for $C_{30}H_{31}N_5O_9S$: 636).

Example 79

In analogy to example 77, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and 1-chloroethyl ethyl carbonate there was obtained 4-[4-methoxy-5-(2-methoxy-phenoxy)-6-(5-methyl-pyridine-2-sulfonylamino)-pyrimidin-2-yl]-pyridine-2-carboxylic acid 1-ethoxycarbonyloxy-ethyl ester as a white solid. ISN mass spectrum, m/e 638.1 (M−1 calculated for $C_{29}H_{29}N_5O_{10}S$: 638).

Example 80

In analogy to example 77, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and cyclohexyl 1-chlorethyl carbonate (synthesis described by A. Riondel et al., Tetrahedron, 1988, Vol. 44, 1619) there was obtained 4-[4-methoxy-5-(2-methoxy-phenoxy)-6-(5-methyl-pyridine-2-sulfonylamino)-pyrimidin-2-yl]-pyridine-2-carboxylic acid 1-cyclohexyloxycarbonyloxy-ethyl ester as a white solid. ISN mass spectrum, m/e 692.1 (M−1 calculated for $C_{33}H_{35}N_5O_{10}S$: 692).

Example 81

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and hydroxyacetone there was obtained 4-[4-methoxy-5-(2-methoxy-phenoxy)-6-(5-methyl-pyridine-2-sulfonylamino)-pyrimidin-2-yl]-pyridine-2-carboxylic acid 2-oxo-propyl ester as a white solid. ISP mass spectrum, m/e 580.1 (M+1 calculated for $C_{27}H_{25}N_5O_8S$: 580).

Example 82

In analogy to example 77, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and 1-chloropinacolone there was obtained 4-[4-methoxy-(5-2-methoxy-phenoxy)-6-(5-methyl-pyridine-2-sulfonylamino)-pyrimidin-2-yl]-pyridine-2-carboxylic acid 3,3-dimethyl-2-oxo-butyl ester as a white solid. ISN mass spectrum, m/e 620.1 (M−1 calculated for $C_{30}H_{31}N_5O_8S$: 620).

Example 83

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and 2-hydroxyacetophenone there was obtained 4-[4-methoxy-5-(2-methoxy-phenoxy)-6-(5-methyl-pyridine-2-sulfonylamino)-pyrimidin-2-yl]-pyridine-2-carboxylic acid 2-oxo-2-phenyl-ethyl ester as a white solid. ISN mass spectrum, m/e 640 (M−1 calculated for $C_{32}H_{27}N_5O_8S$: 640).

Example 84

In analogy to example 77, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and 1-bromo-4-methyl-petan-2-one (synthesis described by Catch et al.: J. Chem. Soc. 1948, 278) there was obtained 4-[4-methoxy-5-(2-methoxy-phenoxy)-6-(5-methyl-pyridine-2-sulfonylamino)-pyrimidin-2-yl]-pyridine-2-carboxylic acid 4-methyl-2-oxo-pentyl ester as a white solid. ISN mass spectrum, m/e 620.1 (M−1 calculated for $C_{30}H_{31}N_5O_8S$: 620).

Example 85

In analogy to example 22, from 4-[4-methoxy-5-(2-methoxy-phenoxy)-6-(5-methyl-pyridine-2-sulfonylamino)-pyrimidin-2-yl]-pyridine-2-carboxylic acid, product of example 21, and dihydroxyacetone there was obtained 4-[4-methoxy-5-(2-methoxy-phenoxy)-6-(5-methyl-pyridine-2-sulfonylamino)-pyrimidin-2-yl]-pyridine-2-carboxylic acid 3-hydroxy-2-oxo-propyl ester as a white solid. ISP mass spectrum, m/e 596.1 (M+1 calculated for $C_{27}H_{25}N_5O_9S$: 596).

Example 86

In analogy to example 77, from 4-[4-methoxy-5-(2-methoxy-phenoxy)-6-(5-methyl-pyridine-2-sulfonylamino)- pyrimidin-2-yl]-pyridine-2-carboxylic acid, product of example 21, and 4-bromo-5-methyl-[1,3]dioxol-2-one (synthesis described by M. Alpegiani et al., Synth. Commun. 1992, Vol. 22, 1277) there was obtained 4-[4-methoxy-5-(2-methoxy-phenoxy)-6-(5-methyl-pyridine-2-sulfonylamino)-pyrimidin-2-yl]-pyridine-2-carboxylic acid 5-methyl-2-oxo-[1,3]dioxol-4-ylmethyl ester as a white solid. ISN mass spectrum, m/e 634.3 (M−1 calculated for $C_{29}H_{25}N_5O_{10}S$: 634).

Example A

Tablets containing the following ingredients can be produced in a conventional manner:

| Ingredients | mg per tablet |
| --- | --- |
| Compound of formula (I) | 10.0–100.0 |
| Lactose | 125.0 |
| Corn starch | 75.0 |
| Talc | 4.0 |
| Magnesium stearate | 1.0 |

Example B

Capsules containing the following ingredients can be produced in a conventional manner:

| Ingredients | mg per capsule |
| --- | --- |
| Compound of formula (I) | 25.0 |
| Lactose | 150.0 |
| Corn starch | 20.0 |
| Talc | 5.0 |

Example C

Injection solutions can have the following composition:

| Compound of formula (I) | 3.0 mg |
| --- | --- |
| Gelatine | 150.0 mg |
| Phenol | 4.7 mg |
| Water for injection | ad 1.0 ml |

Example D 500 mg of compound of formula (I) are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses which can be applied individually.

Described in terms of its preferred embodiments, the skilled artisan upon reading this specification will envision various alternative embodiments. These embodiments are to be considered within the scope and spirit of the subject invention, which is only to be limited by the claims that follow and their equivalents.

What is claimed is:
1. A compound of formula:

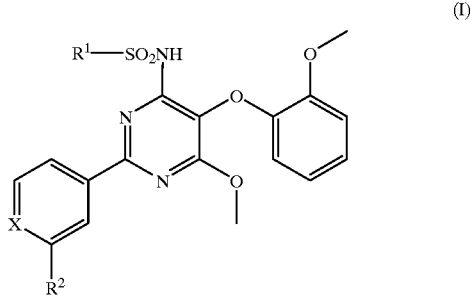

wherein
$R^1$ is pyridyl, pyridyl substituted with halogen, lower alkyl, hydroxy-lower alkyl or lower alkenyl, pyrrolyl, pyrrolyl substituted with halogen, lower alkyl, hydroxy-lower alkyl or lower alkenyl, imidazolyl, imidazolyl substituted with halogen, lower alkyl, hydroxy-lower alkyl or lower alkenyl, thiazolyl, thiazolyl substituted with halogen, lower alkyl, hydroxy-lower alkyl or lower alkenyl, thiazolinyl, thiazolinyl substituted with halogen, lower alkyl, hydroxy-lower alkyl or lower alkenyl, oxazolyl, or oxazolyl substituted with halogen, lower alkyl, hydroxy-lower alkyl or lower alkenyl;

$R^2$ is (i) $R^{21}$, (ii) —Y—$R^{22}$, (iii) heterocyclyl selected from the group consisting of pyrimidinyl, imidazolyl, oxadiazolyl, oxazolyl and thiazolyl, or (iv) heterocyclyl selected from the group consisting of pyrimidinyl, imidazolyl, oxadiazolyl, oxazolyl and thiazolyl, which is mono-, di- or tri-substituted, independently, with hydroxy, lower alkenyl, amino, lower alkanoylamino, lower alkoxycarbonylamino, lower alkyl or hydroxy-lower alkyl;

$R^{21}$ is cyano, hydroxy-lower alkyl, carboxy, —C(O)NR$^a$R$^b$, —(CH$_2$)$_{1-4}$NHR$^c$, —(CH$_2$)$_{1-4}$NHC(O)NH(CH$_2$)$_{0-3}$CH$_3$, amidino, hydroxyamidino, lower alkoxycarbonyl or hydroxy-lower alkoxycarbonyl;

$R^{22}$ is hydrogen, lower alkanoyl, carboxy-lower alkyl, lower alkoxycarbonyl, lower alkoxycarbonyl-lower alkyl, carbamoyl-lower alkyl, di-lower alkylcarbamoyl-lower alkyl, allyl, lower alkyl or hydroxy-lower alkyl;

$R^a$ is hydrogen, lower alkyl, or lower alkyl substituted with hydroxy or lower alkoxy;

$R^b$ is hydrogen or lower alkyl;

$R^c$ is hydrogen, acetyl or lower alkylsulfonyl;

X is —CH— or —N—; and

Y is —O—, —NH—;
or a pharmaceutically acceptable salt or ester thereof.

2. The compound of claim 1, wherein X is —CH—.

3. The compound of claim 1, wherein X is —N—.

4. The compound according to claim 1, wherein $R^1$ is pyridyl, pyridyl substituted with halogen, lower alkyl, hydroxy-lower alkyl or lower alkenyl, thiazolyl, or thiazolyl substituted with halogen, lower alkyl, hydroxy-lower alkyl or lower alkenyl.

5. The compound according to claim 1, wherein $R^1$ is pyridyl, pyridyl substituted with lower alkyl or lower alkenyl, thiazolyl, or thiazolyl substituted with lower alkyl or lower alkenyl.

6. The compound according to claim 1, wherein $R^{21}$ is cyano, hydroxy-lower alkyl, carboxy, lower alkoxycarbonyl,

47

—C(O)NR$^a$R$^b$, —CH$_2$NHR$^c$, amidino, hydroxyamidino or —CH$_2$NHC(O)NHCH$_2$CH$_3$, and R$^a$, R$^b$ and R$^c$ are as defined in claim 1.

7. The compound according to claim 1, wherein R$^{21}$ is cyano, carboxy, carbamoyl, lower alkoxycarbonyl, hydroxy-lower alkyl, acetylaminomethyl or methylsulfonylaminomethyl.

8. The compound according to claim 1, wherein R$^2$ is R$^{21}$, —Y—R$^{22}$ or heterocyclyl selected from the group consisting of 2-pyrimidinyl, 2-imidazolyl, [1,2,4]oxadiazol-3-yl, 2-oxazolyl or 2-thiazolyl, 2-pyrimidinyl mono-, di- or tri-substituted, independently, with lower alkyl, hydroxy-lower alkyl, lower alkenyl, lower alkoxycarbonylamino, lower alkanoylamino, hydroxy or amino, 2-imidazolyl mono-, di- or tri-substituted, independently, with lower alkyl, hydroxy-lower alkyl, lower alkenyl, lower alkoxycarbonylamino, lower alkanoylamino, hydroxy or amino, [1,2,4]oxadiazol-3-yl mono-, di- or tri-substituted, independently, with lower alkyl, hydroxy-lower alkyl, lower alkenyl, lower alkoxycarbonylamino, lower alkanoylamino, hydroxy or amino, 2-oxazolyl mono-, di- or tri-substituted, independently, with lower alkyl, hydroxy-lower alkyl, lower alkenyl, lower alkoxycarbonylamino, lower alkanoylamino, hydroxy or amino, and 2-thiazolyl mono-, di- or tri-substituted, independently, with lower alkyl, hydroxy-lower alkyl, lower alkenyl, lower alkoxycarbonylamino, lower alkanoylamino, hydroxy or amino.

9. The compound according to claim 1, wherein R$^2$ is R$^{21}$, —Y—R$^{22}$ or heterocyclyl selected from the group consisting of 2-pyrimidinyl, 2-imidazolyl, [1,2,4]oxadiazol-3-yl, 2-pyrimidinyl substituted with lower alkyl, isopropenyl, t-butoxycarbonylamino, formylamino, acetylamino, hydroxy, amino or hydroxymethyl, 2-imidazolyl substituted with lower alkyl, isopropenyl, t-butoxycarbonylamino, formylamino, acetylamino, hydroxy, amino or hydroxymethyl, and [1,2,4]oxadiazol-3-yl substituted with lower alkyl, isopropenyl, t-butoxycarbonylamino, formylamino, acetylamino, hydroxy, amino or hydroxymethyl.

10. The compound according to claim 1, wherein R$^{22}$ is hydrogen, lower alkyl, carboxymethyl, lower alkoxycarbonyl-lower alkyl, carbamoylmethyl, dimethylcarbamoylmethyl, hydroxy-lower alkyl or acetyl.

11. The compound according to claim 1, wherein R$^{22}$ is hydrogen, lower alkyl, lower alkoxycarbonyl-lower alkyl or hydroxy-lower alkyl.

12. The compound according to claim 1 which is 5-methyl-pyridine-2-sulfonic acid [2-(2-hydroxymethyl-pyridine-4-yl)-6-methoxy-5-(2-methoxy-phenoxy)-pyrimidin-4-yl]-amide.

13. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid ethyl ester.

14. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid methyl ester.

15. The compound according to claim 1 which is N-hydroxy-4-[4-methoxy-5-(2-methoxy-phenoxy)-6-(5-methyl-pyridine-2-sulfonylamino)-pyrimidin-2-yl]-pyridine-2-carboxamidine.

16. The compound according to claim 1 which is 5-methyl-pyridine-2-sulfonic acid {6-methoxy-5-(2-methoxy-phenoxy)-2-[2-(5-methyl-[1,2,4]oxadiazol-3-yl)-pyridine-4-yl]-pyrimidin-4-yl}-amide.

17. The compound according to claim 1 which is 5-methyl-pyridine-2-sulfonic acid [2-[2-

48

(methanesulfonylamino-methyl)-pyridine-4-yl]-6-methoxy-5-(2-methoxy-phenoxy)-pyrimidin-4-yl]-amide.

18. The compound according to claim 1 which is 5-isopropyl-pyridine-2-sulfonic acid [2-[2-methanesulfonylamino-methyl)-pyridine-4-yl]-6-methoxy-5-(2-methoxy-phenoxy)-pyrimidin-4-yl]-amide.

19. The compound according to claim 1 which is 5-isopropyl-pyridine-2-sulfonic acid {6-methoxy-5-(2-methoxy-phenoxy)-2-[2-(5-methyl-[1,2,4]oxadiazol-3-yl)-pyridine-4-yl]-pyrimidin-4-yl}-amide.

20. The compound according to claim 1 which is 5-methyl-pyridine-2-sulfonic acid [2-(2-cyano-pyridine-4-yl)-6-methoxy-5-(2-methoxy-phenoxy)-pyrimidin-4-yl]-amide.

21. The compound according to claim 1 which is 5-methyl-pyridine-2-sulfonic acid [2-(3-hydroxy-phenyl)-6-methoxy-5-(2-methoxy-phenoxy)-pyrimidin-4-yl]-amide.

22. The compound according to claim 1 which is 5-methyl-pyridine-2-sulfonic acid [2-[3-(2-hydroxy-ethoxy)-phenyl]-6-methoxy-5-(2-methoxy-phenoxy)-pyrimidin-4-yl]-amide.

23. The compound according to claim 1 which is 5-isopropyl-pyridine-2-sulfonic acid [2-[2-(2-hydroxy-ethoxy)-pyridine-4-yl]-6-methoxy-5-(2-methoxy-phenoxy)-pyrimidin-4-yl]-amide.

24. The compound according to claim 1 which is 5-methyl-pyridine-2-sulfonic acid [2-(2-hydroxy-pyridin-4-yl)-6-methoxy-5-(2-methoxy-phenoxy)-pyrimidin-4-yl]-amide.

25. The compound according to claim 1 which is {3-[4-methoxy-5-(2-methoxy-phenoxy)-6-(5-methyl-pyridine-2-sulfonylamino)-pyrimidin-2-yl]-phenoxy}-acetic acid ethyl ester.

26. The compound according to claim 1 which is 5-isopropyl-pyridine-2-sulfonic acid [2-(2-hydroxymethyl-pyridin-4-yl)-6-methoxy-5-(2-methoxy-phenoxy)-pyrimidin-4-yl]-amide.

27. The compound according to claim 1 which is N-{4-[4-(5-isopropyl-pyridine-2-sulfonylamino)-6-methoxy-5-(2-methoxy-phenoxy)-pyrimidin-2-yl]-pyridin-2-ylmethyl}-acetamide.

28. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid.

29. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid isopropyl ester.

30. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid ethyl ester.

31. The compound according to claim 1 which is 5-methyl-thiazole-2-sulfonic acid [2-[2-(2-hydroxy-ethoxy)-pyridin-4-yl]-6-methoxy-5-(2-methoxy-phenoxy)-pyrimidin-4-yl]-amide.

32. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid amide.

33. The compound according to claim 1 which is N-hydroxy-4-[4-(5-isopropyl-pyridine-2-sulfonylamino)-6-methoxy-5-(2-methoxy-phenoxy)-pyrimidin-2-yl]-pyridine-2-carboxamidine.

34. The compound according to claim 1 which is acetic acid 3-[4-methoxy-5-(2-methoxy-phenoxy)-6-(5-methyl-pyridine-2-sulfonylamino)-pyrimidin-2-yl]-phenyl ester.

35. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid methyl ester.

36. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

37. The compound according to claim 1 which is 5-methyl-pyridine-2-sulfonic acid [2-[3-(2-hydroxy-ethoxy)-phenyl]-6-methoxy-5-(2-methoxy-phenoxy)-pyrimidin-4-yl]-amide.

38. The compound according to claim 1 which is 5-methyl-pyridine-2-sulfonic acid [2-(2-cyano-pyridin-4-yl)-6-methoxy-5-(2-methoxy-phenoxy)-pyrimidin-4-yl]-amide.

39. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid.

40. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid methyl ester.

41. The compound according to claim 1 which is 5-methyl-pyridine-2-sulfonic acid [2-(2-hydroxymethyl-pyridin-4-yl)-6-methoxy-5-(2-methoxy-phenoxy)-pyrimidin-4-yl]-amide.

42. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid ethyl ester.

43. The compound according to claim 1 which is 5-isopropyl-pyridine-2-sulfonic acid [2-(2-hydroxymethyl-pyridin-4-yl)-6-methoxy-5-(2-methoxy-phenoxy)-pyrimidin-4-yl]-amide.

44. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid amide.

45. The compound according to claim 1 which is 4-[4-(5-isopropyl-pyridine-2-sulfonylamino)-6-methoxy-5-(2-methoxy-phenoxy)-pyrimidin-2-yl]-pyridine-2-carboxylic acid ethyl ester.

46. The compound according to claim 1 which is 5-methyl-pyridine-2-sulfonic acid {6-methoxy-5-(2-methoxy-phenoxy)-2-[2-(5-methyl-[1,2,4]oxadiazol-3-yl)-pyridin-4-yl]-pyrimidin-4-yl}-amide.

47. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

48. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid.

49. The compound according to claim 1 which is 5-methyl-pyridine-2-sulfonic acid [2-(3-hydroxy-phenyl)-6-methoxy-5-(2-methoxy-phenoxy)-pyrimidin-4-yl]-amide.

50. The compound according to claim 1 which is 5-methyl-pyridine-2-sulfonic acid [2-(2-hydroxymethyl-pyridin-4-yl)-6-methoxy-5-(2-methoxy-phenoxy)-pyrimidin-4-yl]-amide.

51. The compound according to claim 1 which is 4-[4-methoxy-5-(2-methoxy-phenoxy)-6-(5-methyl-pyridine-2-sulfonylamino)-pyrimidin-2-yl]-pyridine-2-carboxylic acid 1-acetoxy-ethyl ester.

52. A compound of formula:

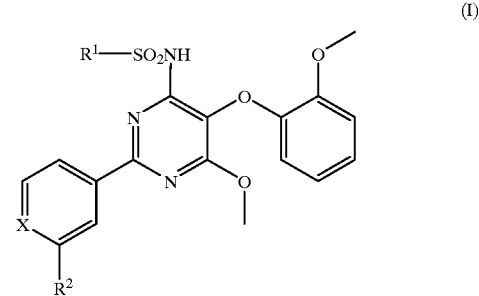

(I)

wherein $R^1$ is pyridyl or pyridyl substituted with lower alkyl;

$R^2$ is hydroxy, carboxy or methoxycarbonyl; and

X is —CH— or —N—;

or a pharmaceutically acceptable salt or ester thereof.

53. The compound according to claim 52, wherein $R^1$ is pyridyl substituted with lower alkyl.

54. The compound according to claim 53, wherein $R^1$ is methylpyridyl.

55. The compound according to claim 54, wherein $R^1$ is 5-methyl-pyridine-2-yl.

56. The compound according to claim 55, wherein $R^2$ is hydroxy.

57. The compound according to claim 56, wherein X is —CH—.

58. The compound according to claim 57 which is 5-methyl-pyridine-2-sulfonic acid [2-(3-hydroxy-phenyl)-6-methoxy-5-(2-methoxy-phenoxy)-pyrimidin-4-yl]-amide.

59. The compound according to claim 55, wherein X is —N—.

60. The compound according to claim 59, wherein $R^2$ is carboxy.

61. The compound according to claim 60 which is 4-[4-methoxy-5-(2-methoxy-phenoxy)-6-(5-methyl-pyridine-2-sulfonylamino)-pyrimidin-2-yl]-pyridine-2-carboxylic acid.

62. The compound according to claim 59, wherein $R^2$ is methoxycarbonyl.

63. The compound according to claim 60 which is 4-[4-methoxy-5-(2-methoxy-phenoxy)-6-(5-methyl-pyridine-2-sulfonylamino)-pyrimidin-2-yl]-pyridine-2-carboxylic acid methyl ester.

* * * * *